(12) United States Patent
Pisarchik et al.

(10) Patent No.: US 7,071,161 B2
(45) Date of Patent: Jul. 4, 2006

(54) VARIANTS OF CORTICOTROPIN RELEASING HORMONE RECEPTOR TYPE 1 AND USES THEREOF

(75) Inventors: Alexander Pisarchik, Cordova, TN (US); Andrzej Slominski, Germantown, TN (US)

(73) Assignee: The University of Tennessee Research Corporation, Knoxville, TN (US)

( * ) Notice: Subject to any disclaimer, the term of this patent is extended or adjusted under 35 U.S.C. 154(b) by 599 days.

(21) Appl. No.: 10/242,822

(22) Filed: Sep. 13, 2002

(65) Prior Publication Data

US 2003/0113799 A1  Jun. 19, 2003

Related U.S. Application Data

(60) Provisional application No. 60/322,195, filed on Sep. 14, 2001.

(51) Int. Cl.
*C07K 14/72* (2006.01)
*A61K 38/16* (2006.01)

(52) U.S. Cl. .................. 514/12; 530/350; 530/306
(58) Field of Classification Search ................ 530/350, 530/306; 514/12; 536/23.1
See application file for complete search history.

(56) References Cited

U.S. PATENT DOCUMENTS 6,638,905 B1 * 10/2003 Perrin et al.

OTHER PUBLICATIONS

Liaw et al., Localization of ligand-binding domains of human corticotropin-releasing factor receptor: A chimeric receptor approach, Mol. Endocrinol. 11:980-985, 1997.*
Perrin et al., Corticotropin releasing factor receptors and their ligand family, Ann. New York Acad. Sci., 885:312-328, Oct. 1999.*
Pisarchik et al., Alternative splicing of CRH-R1 receptors in human and mouse skin: identification of new variants and their differential expression, FASEB J. 15(14):2754-2756, Dec. 2001.*
Sakai et al., The genomic organizationof the human corticotropin-releasing factor type-1 receptor, Gene, 219:125-130, 1998.*

* cited by examiner

*Primary Examiner*—Elizabeth Kemmerer
*Assistant Examiner*—Claire M. Kaufman
(74) *Attorney, Agent, or Firm*—Benjamin Aaron Adler

(57) ABSTRACT

The present invention identifies four new isoforms of human corticotropin releasing hormone receptor type 1 (CRH-R1e, 1f, 1g and 1h) and three new isoforms of mouse corticotropin releasing hormone receptor type 1 (mCRH-R1c, 1e and 1f). The data indicate that polymorphism of CRH-R1 expression is related to anatomic location, skin physiological or pathological status, specific cell type, external stress (UV), and that cAMP dependent pathways and TPA may regulate CRH-R1.

2 Claims, 16 Drawing Sheets

CRH-R1 isoforms:

```
hCRH-R1α    MGGHPQLRLVKALLLLGLNPVSASLQDQHCESLSLASNISGLQCNASVDLIGTCWPRSPAGQLVVRPCPAFFYGVRYNTT  80
hCRH-R1β    MGGHPQLRLVKALLLLGLNPVSASLQDQHCESLSLASNISGLQCNASVDLIGTCWPRSPAGQLVVRPCPAFFYGVRYNTT  80
hCRH-R1c    MGGHPQLRLVKALLLLGLNPVSASLQDQHCESLSLASNIS----------------------------------------  40
hCRH-R1d    MGGHPQLRLVKALLLLGLNPVSASLQDQHCESLSLASNISGLQCNASVDLIGTCWPRSPAGQLVVRPCPAFFYGVRYNTT  80
hCRH-R1e1   MGGHPQLRLVKALLLLGLNPVSASLQDQHCESLSLASNISEKKQGALPCRSHHQLPGP-YLPGGPPGGLCPLSAAQEHPV  80
hCRH-R1f    MGGHPQLRLVKALLLLGLNPVSASLQDQHCESLSLASNISGLQCNASVDLIGTCWPRSPAGQLVVRPCPAFFYGVRYNTT  80
hCRH-R1g    MGGHPQLRLVKALLLLGLNPVSASLQDQHCESLSLASNISGLQCNASVDLIGTCWPRSPAGQLVVRPCPAFFYGVRYNTT  80
hCRH-R1h    MGGHPQLRLVKALLLLGLNPVSASLQDQHCESLSLASNISGLQCNASVDLIGTCWPRSPAGQLVVRPCPAFFYGVRYNTT  80
mCRH-R1α    MGQRPQLRLVKALLLGLNPVSTSLQDQQCESLSLASNVS-----------------------------------------  40
mCRH-R1c    MGQRPQLRLVKALLLGLNPVSTSLQDQQCESLSLASNVSEEEQSALPHCRHHQLPGPLHLPGPPGGLCPLPAAQEHPV   80
mCRH-R1e1   MGQRPQLRLVKALLLGLNPVSTSLQDQQCESLSLASNVSGLQCNASVDLIGTCWPRSPAGQLVVRPCPAFFYGVRYNTT  80
mCRH-R1f    MGQRPQLRLVKALLLGLNPVSTSLQDQQCESLSLASNVSGLQCNASVDLIGTCWPRSPAGQLVVRPCPAFFYGVRYNTT  80
```

```
           ########-1-########
hCRH-R1α    NNGYRECLANGSWAARVNYSECQEILNEEKKSKVHYHVAVIINYLGHCISLVALLVAFVLFLRL---------------  -44
hCRH-R1β    NNGYRECLANGSWAARVNYSECQEILNEEKKSKVHYHVAVIINYLGHCISLVALLVAFVLFLRLRPGCTHWGDQADGALE 160
hCRH-R1c    DNGYRECLANGSWAARVNYSECQEILNEEKKSKVHYHVAVIINYLGHCISLVALLVAFVLFLRL---------------  104/64
hCRH-R1d    NNGYRECLANGSWAARVNYSECQEILNEEKKSKVHYHVAVIINYLGHCISLVALLVAFVLFLRL---------------  144
hCRH-R1e1   EKKQGALPCRSHHQLPGPLYLPGGPPGGLCPLSAAQEHPVPAKHHPLEPHLRLHPAQRHLVRGPANHEPRGPPEQRGLVQ 160
hCRH-R1f    NNGYRECLANGSWAARVNYSECQEILNEEKKSKVHYHVAVIINYLGHCISLVALLVAFVLFLRL---------------  144
hCRH-R1g    NNGYRECLANGSWAARVNYSECQEILNEEKKSKVHYHVAVI-NYLGHCISLVALLVAFVLFLRL---------------  -44
hCRH-R1h    NNGYRECLANGSWAARVNYSECQEILNEEEPGTQAPGRAHRGGT                                     125
                                                        (SEQ ID NO. 8)

mCRH-R1α    NNGYRECLANGSWAARVNYSECQEILNEEKKSKVHYHIAVIINYLGHCISLVALLVAFVLFLRL---------------  144
mCRH-R1c    DNGYRECLANGSWAARVNYSECQEILNEEKKSKVHYHIAVIINYLGHCISLVALLVAFVLFLRL---------------  104
mCRH-R1e1   PEEHHPLEPHLGFHPAQRHVVCGPAHREPRGPPEQRGLVQAGDSRLQLLPRNQLLLDVR                      139
                                                        (SEQ ID NO. 11)

mCRH-R1e2   MSIKKSKVHYHIAVIINYLGHCISLVALLVAFVLFLRL---------------                            38
mCRH-R1f    NNGYRECLANGSWAARVNYSECQEILNEEKKSKVHYHIAVIINYLGHCISLVALLVAFVLFLRL---------------  144
```

Fig. 5A

```
hCRH-R1α    ---------RSIRCLRNIIHWNLISAFILRNATWFVVQLTMSPEVHQSNVGWCRLVTAAYNYFHVTNFFWMFGEGC  211
hCRH-R1β    VGAPWSGAPFQVVRRSIRCLRNIIHWNLISAFILRNATWFVVQLTMSPEVHQSNVGWCRLVTAAYNYFHVTNFFWMFGEGC  240
hCRH-R1c    ---------RSIRCLRNIIHWNL-ISAFILRNATWFVVQLTMSPEVHQSNVGWCRLVTAAYNYFHVTNFFWMFGEGC  171
hCRH-R1d    ---------RSIRCLRNIIHWNLISAFILRNATWFVVQLTMSPEVHQSNVGWCRLVTAAYNYFHVTNFFWMFGEGC  211
hCRH-R1e1   VGDSRLQLLPCDQLLLDVRRGLLPAHSHRAHLLH                                              194
                                                                              (SEQ ID NO. 5)
hCRH-R1e2                                      MSPEVHQSNVGWCRLVTAAYNYFHVTNFFWMFGEGC  36
hCRH-R1f    ---------RSIRCLRNIIHWNLISAFILRNATWFVVQLTMSPEVHQSNVGWCRLVTAAYNYFHVTNFFWMFGEGC  211
hCRH-R1g    ---------RSIRCLRNIIHWNLISAFILRNATWFVVQLTMSPEVHQSNVGWCRLVTAAYNYFHVTNFFWMFGEGC  211
mCRH-R1α    ---------RSIRCLRNIIHWNLISAFILRNATWFVVQLTVSPEVHQSNVAWCRLVTAAYNYFHVTNFFWMFGEGC  211
mCRH-R1c    ---------RSIRCLRNIIHWNLISAFILRNATWFVVQLTVSPEVHQSNVAWCRLVTAAYNYFHVTNFFWMFGEGC  171
mCRH-R1e2                                      MSPEVHQSNVAWCRLVTAAYNYFHVTNFFWMFGEGC  105
mCRH-R1f    ---------RSIRCLRNIIHWNLISAF-LRNATWFVVQLTVSPEVHQSNVAWCRLVTAAYNYFHVTNFFWMFGEGC  211 hCRH-R1α    YLHTAIVLTYSTDRLRKWMFICIGWGVPFPIIVAWAIGKLYYDNEKCWFGKRPGVYTDYIYQGPMILVLLINFIFLFNIV  291
hCRH-R1β    YLHTAIVLTYSTDRLRKWMFICIGWGVPFPIIVAWAIGKLYYDNEKCWFGKRPGVYTDYIYQGPMILVLLINF-FLFNIV  320
hCRH-R1c    YLHTAIVLTYSTDRLRKWMFICIGWGVPFPIIVAWAIGKLYYDNEKCWFGKRPGVYTDYIYQGPMILVLLINFIFLFNIV  251
hCRH-R1d    YLHTAIVLTYSTDRLRKWMFICIGWGVPFPIIVAWAIGKLYYDNEKCWFGKRPGVYTDYIYQGPMILVLLINFIFLFNIV  291
hCRH-R1e2   YLHTAIVLTYSTDRLRKWMFICIGWGVPFPIIVAWAIGKLYYDNEKCWFGKRPGVYTDYIYQGPMILVLLINFIFLFNIV  116
hCRH-R1-f   YLHTAIVLTYSTDRLRKWMFICIGWGVPFPIIVAWAIGKLYYDNEKCWFGKRPGVYTDYIYQGPMILVLLINFIFLFNIV  291
hCRH-R1-g   YLHTAIVLTYSTDRLRKWMFICIGWGVPFPIIVAWAIGKLYYDNEKCWFGKRPGVYTDYIY------------------  272
mCRH-R1α    YLHTAIVLTYSTDRLRKWMFVCIGWGVPFPIIVAWAIGKLYYDNEKCWFGKRPGVYTDYIYQGPMILVLLINFIFLFNIV  291
mCRH-R1c    YLHTAIVLTYSTDRLRKWMFVCIGWGVPFPIIVAWAIGKLYYDNEKCWFGKRPGVYTDYIYQGPMILVLLINFIFLFNIV  251
mCRH-R1e    YLHTAIVLTYSTDRLRKWMFVCIGWGVPFP-IVAWAIGKLYYDNEKCWFGKRPGVYTDYIYQGPMILVLLINFIFLFNIV  185
mCRH-R1f    YLHTAIVLTYSTDRLRKWMFVCIGWGVPFPIIVAWAIGKLYYDNEKCWFGKRPGVYTDYIYQGPMILVLLINFIFLFNIV  291
```

Fig. 5B

```
                  →            ########-6-########              ####  ↓###-7-#####  ↓#
hCRH-R1α    RILMTKLRASTTSETIQYRKAVKATLVLLPLLGITYMLFFVNPGEDEVSRVVFIYENSFLESFQGFFVSVFYCFLNSEVR 371
hCRH-R1β    RILMTKLRAST-SETIQYRKAVKATLVLLP-LGITYMLFFVNPGEDEVSRVVFIYENSFLESFQGFFVSVFYCFLNSEVR 400
hCRH-R1c    RILMTKLRASTTSETIQYRKAVKATLVLLPLLGITYMLFFVNPGEDEVSRVVFIYENSFLESFQGFFVSVFYCFLNSEVR 331
hCRH-R1d    RILMTKLRASTTSETIQYRKAVKATLVLLPLLGITYMLFFVNPGEDEVSRVVFIYENSFLESFQ--------------VR 357
hCRH-R1e2   RILMTKLRASTTSETIQYRKAVKATLVLLPLLGITYMLFFVNPGEDEVSRVVFIYENSFLESFQGFFVSVFYCFLNSEVR -96
hCRH-R1f    RILMTKLRASTTSETIQYRKAVKATLVLLPLLGITYMLFFVNPGEDEVSRVVFIYENSFLESFQGFFVSVFYCFLNSEVR 370
hCRH-R1g    RILMTKLRASTTSETIQYRASLCLCSTVSSIVRSVLPSGRGGTGGRTSTRSVPEWPVPCPSPPPQPVSAFTASSSPQQS
                                                                                      (SEQ ID NO. 6)
mCRH-R1α    RILMTKLRASTTSETIQYRKAVKATLVLLPLLGITYMLFFVNPGEDEVSRVVFIYENSFLESFQGFFVSVFYCFLNSEVR 297
mCRH-R1c    RILMTKLRASTTSETIQYRKAVKATLVLLPLLGITYMLFFVNPGEDEVSRVVFIYENSFLESFQGFFVSVFYCFLNSEVR 371
mCRH-R1e    RILMTKLRASTTSETIQYRKAVKATLVLLPLLGITYMLFFVNPGEDEVSRVVFIYENSFLESFQGFFVSVFYCFLNSEVR 331
mCRH-R1f    RILMTKLRASTTSETIQYRSSCLCSIVF                                                     265
                                                                                              319
                                                                                      (SEQ ID NO. 12)

hCRH-R1α    SAIRKRWHRWQDKHSIRARVARAMSIPTSPTRVSFHSIKQSTAV 415  (SEQ ID NO.  1)
hCRH-R1β    SAIRKRWHRWQDKHSIRARVARAMSIPTSPTRVSFHSIKQSTAV 444  (SEQ ID NO.  2)
hCRH-R1c    SAIRKRWHRWQDKHSIRARVARAMSIPTSPTRVSFHSIKQSTAV 375  (SEQ ID NO.  3)
hCRH-R1d    SAIRKRWHRWQDKHSIRARVARAMSIPTSPTRVSFHSIKQSTAV 401  (SEQ ID NO.  4)
hCRH-R1e2   SAIRKRWHRWQDKHSIRARVARAMSIPTSPTRVSFHSIKQSTAV 240  (SEQ ID NO. 14)
hCRH-R1f    SAIRKRWHRWQDKHSIRARVARAMSIPTSPTRVSFHSIKQSTAV 341  (SEQ ID NO.  7)
hCRH-R1g    SAIRKRWRRWQDKHSIRARVARAMSIPTSPTRVSFHSIKQSTAV 415  (SEQ ID NO.  9)
mCRH-R1α    SAIRKRWRRWQDKHSIRARVARAMSIPTSPTRVSFHSIKQSTAV 375  (SEQ ID NO. 10)
mCRH-R1c    SAIRKRWRRWQDKHSIRARVARAMSIPTSPTRVSFHSIKQSTAV 309  (SEQ ID NO. 13)
```

Fig. 5C

```
CRH-R1e  MGQRPQLPLVKALLLLGLNPVSTTLQDQRCESLSLASNVSEEKQSALPHCRHHQLPGPLHLPGSPLGGLCPLSASQEHPV  80
CRH-R1f  MGQRPQLPLVKALLLLGLNPVSTTLQDQRCESLSLASNVSGPQCNASVDLIGTCWPRSPAGQLVVRPCPAFFYGVRYNTT  80
CRH-R1h  MGQRPQLPLVKALLLLGLNPVSTTLQDQRCESLSLASNVSGPQCNASVDLIGTCWPRSPAGQLVVRPCPAFFYGVRYNTT  80
CRH-R1j  MGQRPQLPLVKALLLLGLNPVSTTLQDQRCESLSLASNVSGPQCNASVDLIGTCWPRSPAGQLVVRPCPAFFYGVRYNTT  80
CRH-R1k  MGQRPQLPLVKALLLLGLNPVSTTLQDQRCESLSLASNVSGPQCNASVDLIGTCWPRSPAGQLVVRPCPAFFYGVRYNTT  80
CRH-R1m  MGQRPQLPLVKALLLLGLNPVSTTLQDQRCESLSLASNVSGPQCNASVDLIGTCWPRSPAGQLVVRPCPAFFYGVRYNTT  80
CRH-R1n  MGQRPQLPLVKALLLLGLNPVSTTLQDQRCESLSLASNVSGPQCNASVDLIGTCWPRSPAGQLVVRPCPAFFYGVRYNTT  80

CRH-R1e  PEEHHPLEPHLGFHPAQCHVVCGPAHHEPRGPPEOCGMVQVGDSCLQLFPRHQLLLDVW..................... 139
CRH-R1f  NNGYRECLANGSWAARVNYSECQEILNEEEHPVPEEHHPLEPHLGFHPAQCHVVCGPAHHEPRGPPEOCGMVQVGDSCLQ 160
CRH-R1h  NNGYRECLANGSWAARVNYSECQEILNEEEWLRM.............................................  114
CRH-R1j  NNGYRECLANGSWAARVNYSECQEILNEEEHPVPEEHHPLEPHLGFHPAQCHVVCISLVALLVAFVLFLRLRSIRCLRNIIHWNLIS  160
CRH-R1k  NNGYRECLANGSWAARVNYSECQEILNEEEHPVPEEHHPLEPHLGFHPAQCHVVCISLVALLVAFVLFLRLRSIRCLRNIIHWNLIS  160
CRH-R1m  NNGYRECLANGSWAARVNYSECQEILNEEEHPVPEEHHPLEPHLGFHPAQCHVVCISLVALLVAFVLFLRLRSIRCLRNIIHWNLIS  160
CRH-R1n  NNGYRECLANGSWAARVNYSECQEILNEEEHPVPEEHHPLEPHLGFHPAQCHVVCISLVALLVAFVLFLRLRSIRCLRNIIHWNLIS  160
         #-2-########                                                 ########-1-#########

CRH-R1e  ................................................................................
CRH-R1f  AFILRNATWFVVQLTMSPEVHQSNVGWCRLVTAAYNYFHVTNFFWMFGEGCYLHTAIVPTYSTDRLRKWMFVCIGWGVPF  240
CRH-R1h  ................................................................................
CRH-R1j  LFPRHQLLLDVW....................................................................  172
CRH-R1k  AFILRNATWFVVQLTMSPEVHQSNVGWCRLVTAAYNYFHVTNFFWMFGEGCYLHTAIVPTYSTDRLRKWMFVCIGWGVPF  240
CRH-R1m  AFILRNATWFVVQLTMSPEVHQSNVGWCRLVTAAYNYFHVTNFFWMFGEGCYLHTAIVPTYSTDRLRKWMFVCIGWGVPF  240
CRH-R1n  AFILRNATWFVVQLTMSPEVHQSNVGWCRLVTAAYNYFHVTNFFWMFGEGCYLHTAIVPTYSTDRLRKWMFVCIGWGVPF  240
         ########-3-#########                                     ##########-4-#
```

Fig. 5D

```
CRH-R1e  PIIVAWAIGKLYYDNEKCWFGKRPGVYTDYIYQGPMILVLLINFIFLFNIVRILMTKLRASTTSETIQYRTSLCLCSTVF 320
CRH-R1f  ................................................................................ 320
CRH-R1h  ................................................................................ 320
CRH-R1j  ............................................................................... 281
CRH-R1k  PIIVAWAIGKLYYDNEKCWFGKRPGVYTDYIYQGPMILVLEGCEGHSGAAAPPGHHLHVILCQPWGGRGLQGRLHLLQL 320
CRH-R1m  PIIVAWAIGKLYYDNEKCWFGKRPGVYTDYIYQGPMILVLLINFIFLFNIVRILMTKLRASTTSETIQYRSALPSGRGGI 320
CRH-R1n  PIIVAWAIGKLYYDNEKCWFGKRPGVYTDYIYQGPMILVLL---------------------------------
         ################-5-##############
                                              →
CRH-R1e  ................................................................
CRH-R1f  ................................................................
CRH-R1h  ................................................................
CRH-R1j  ................................................................
CRH-R1k  FPGVLPGLLCVCVLLFSEQ.                                              339
CRH-R1m  GGRISTRSEPEWPAPCPSPSPPPPESASTASSKPQQC.                            356
CRH-R1n  ---------------VRSAIRKRWHRWQDKHSIRARVARAMSIPTS                    312
         #-6-############           ##############-7-###########

CRH-R1e  ................   (SEQ ID NO. 31)
CRH-R1f  ................   (SEQ ID NO. 32)
CRH-R1h  ................   (SEQ ID NO. 33)
CRH-R1j  ................   (SEQ ID NO. 34)
CRH-R1k  ................   (SEQ ID NO. 35)
CRH-R1m  ................   (SEQ ID NO. 36)
CRH-R1n  PTRVSFHSIKQATAV 327 (SEQ ID NO. 37)
```

Fig. 5E

SEQUENCE LISTING

```
<160> NUMBER OF SEQ ID NOS: 49

<210> SEQ ID NO 1
<211> LENGTH: 415
<212> TYPE: PRT
<213> ORGANISM: Homo sapiens
<220> FEATURE:
<223> OTHER INFORMATION: amino acid sequence of human CRH-R1 alpha
      gene: GenBank Accession No. L23332

<400> SEQUENCE: 1

Met Gly Gly His Pro Gln Leu Arg Leu Val Lys Ala Leu Leu Leu
                 5                  10                  15

Leu Gly Leu Asn Pro Val Ser Ala Ser Leu Gln Asp Gln His Cys
                20                  25                  30

Glu Ser Leu Ser Leu Ala Ser Asn Ile Ser Gly Leu Gln Cys Asn
```

```
                          35                  40                  45
Ala Ser Val Asp Leu Ile Gly Thr Cys Trp Pro Arg Ser Pro Ala
                 50                  55                  60
Gly Gln Leu Val Val Arg Pro Cys Pro Ala Phe Phe Tyr Gly Val
                 65                  70                  75
Arg Tyr Asn Thr Thr Asn Asn Gly Tyr Arg Glu Cys Leu Ala Asn
                 80                  85                  90
Gly Ser Trp Ala Ala Arg Val Asn Tyr Ser Glu Cys Gln Glu Ile
                 95                 100                 105
Leu Asn Glu Glu Lys Lys Ser Lys Val His Tyr His Val Ala Val
                110                 115                 120
Ile Ile Asn Tyr Leu Gly His Cys Ile Ser Leu Val Ala Leu Leu
                125                 130                 135
Val Ala Phe Val Leu Phe Leu Arg Leu Arg Ser Ile Arg Cys Leu
                140                 145                 150
Arg Asn Ile Ile His Trp Asn Leu Ile Ser Ala Phe Ile Leu Arg
                155                 160                 165
Asn Ala Thr Trp Phe Val Val Gln Leu Thr Met Ser Pro Glu Val
                170                 175                 180
His Gln Ser Asn Val Gly Trp Cys Arg Leu Val Thr Ala Ala Tyr
                185                 190                 195
Asn Tyr Phe His Val Thr Asn Phe Phe Trp Met Phe Gly Glu Gly
                200                 205                 210
Cys Tyr Leu His Thr Ala Ile Val Leu Thr Tyr Ser Thr Asp Arg
                215                 220                 225
Leu Arg Lys Trp Met Phe Ile Cys Ile Gly Trp Gly Val Pro Phe
                230                 235                 240
Pro Ile Ile Val Ala Trp Ala Ile Gly Lys Leu Tyr Tyr Asp Asn
                245                 250                 255
Glu Lys Cys Trp Phe Gly Lys Arg Pro Gly Val Tyr Thr Asp Tyr
                260                 265                 270
Ile Tyr Gln Gly Pro Met Ile Leu Val Leu Leu Ile Asn Phe Ile
                275                 280                 285
Phe Leu Phe Asn Ile Val Arg Ile Leu Met Thr Lys Leu Arg Ala
                290                 295                 300
Ser Thr Thr Ser Glu Thr Ile Gln Tyr Arg Lys Ala Val Lys Ala
                305                 310                 315
Thr Leu Val Leu Leu Pro Leu Leu Gly Ile Thr Tyr Met Leu Phe
                320                 325                 330
Phe Val Asn Pro Gly Glu Asp Glu Val Ser Arg Val Val Phe Ile
                335                 340                 345
Tyr Phe Asn Ser Phe Leu Glu Ser Phe Gln Gly Phe Phe Val Ser
                350                 355                 360
Val Phe Tyr Cys Phe Leu Asn Ser Glu Val Arg Ser Ala Ile Arg
                365                 370                 375
Lys Arg Trp His Arg Trp Gln Asp Lys His Ser Ile Arg Ala Arg
                380                 385                 390
Val Ala Arg Ala Met Ser Ile Pro Thr Ser Pro Thr Arg Val Ser
                395                 400                 405
Phe His Ser Ile Lys Gln Ser Thr Ala Val
                410                 415

<210> SEQ ID NO 2
```

-continued

<211> LENGTH: 444
<212> TYPE: PRT
<213> ORGANISM: Homo sapiens
<220> FEATURE:
<223> OTHER INFORMATION: amino acid sequence of human CRH-R1 beta
      gene: GenBank Accession No. L23333

<400> SEQUENCE: 2

```
Met Gly Gly His Pro Gln Leu Arg Leu Val Lys Ala Leu Leu Leu
                 5                  10                  15

Leu Gly Leu Asn Pro Val Ser Ala Ser Leu Gln Asp Gln His Cys
                20                  25                  30

Glu Ser Leu Ser Leu Ala Ser Asn Ile Ser Gly Leu Gln Cys Asn
                35                  40                  45

Ala Ser Val Asp Leu Ile Gly Thr Cys Trp Pro Arg Ser Pro Ala
                50                  55                  60

Gly Gln Leu Val Val Arg Pro Cys Pro Ala Phe Phe Tyr Gly Val
                65                  70                  75

Arg Tyr Asn Thr Thr Asn Asn Gly Tyr Arg Glu Cys Leu Ala Asn
                80                  85                  90

Gly Ser Trp Ala Ala Arg Val Asn Tyr Ser Glu Cys Gln Glu Ile
                95                 100                 105

Leu Asn Glu Glu Lys Lys Ser Lys Val His Tyr His Val Ala Val
               110                 115                 120

Ile Ile Asn Tyr Leu Gly His Cys Ile Ser Leu Val Ala Leu Leu
               125                 130                 135

Val Ala Phe Val Leu Phe Leu Arg Leu Arg Pro Gly Cys Thr His
               140                 145                 150

Trp Gly Asp Gln Ala Asp Gly Ala Leu Glu Val Gly Ala Pro Trp
               155                 160                 165

Ser Gly Ala Pro Phe Gln Val Arg Arg Ser Ile Arg Cys Leu Arg
               170                 175                 180

Asn Ile Ile His Trp Asn Leu Ile Ser Ala Phe Ile Leu Arg Asn
               185                 190                 195

Ala Thr Trp Phe Val Val Gln Leu Thr Met Ser Pro Glu Val His
               200                 205                 210

Gln Ser Asn Val Gly Trp Cys Arg Leu Val Thr Ala Ala Tyr Asn
               215                 220                 225

Tyr Phe His Val Thr Asn Phe Phe Trp Met Phe Gly Glu Gly Cys
               230                 235                 240

Tyr Leu His Thr Ala Ile Val Leu Thr Tyr Ser Thr Asp Arg Leu
               245                 250                 255

Arg Lys Trp Met Phe Ile Cys Ile Gly Trp Gly Val Pro Phe Pro
               260                 265                 270

Ile Ile Val Ala Trp Ala Ile Gly Lys Leu Tyr Tyr Asp Asn Glu
               275                 280                 285

Lys Cys Trp Phe Gly Lys Arg Pro Gly Val Tyr Thr Asp Tyr Ile
               290                 295                 300

Tyr Gln Gly Pro Met Ile Leu Val Leu Leu Ile Asn Phe Ile Phe
               305                 310                 315

Leu Phe Asn Ile Val Arg Ile Leu Met Thr Lys Leu Arg Ala Ser
               320                 325                 330

Thr Thr Ser Glu Thr Ile Gln Tyr Arg Lys Ala Val Lys Ala Thr
               335                 340                 345

Leu Val Leu Leu Pro Leu Leu Gly Ile Thr Tyr Met Leu Phe Phe
```

-continued

```
                    350                 355                 360
Val Asn Pro Gly Glu Asp Glu Val Ser Arg Val Val Phe Ile Tyr
                365                 370                 375
Phe Asn Ser Phe Leu Glu Ser Phe Gln Gly Phe Phe Val Ser Val
                380                 385                 390
Phe Tyr Cys Phe Leu Asn Ser Glu Val Arg Ser Ala Ile Arg Lys
                395                 400                 405
Arg Trp His Arg Trp Gln Asp Lys His Ser Ile Arg Ala Arg Val
                410                 415                 420
Ala Arg Ala Met Ser Ile Pro Thr Ser Pro Thr Arg Val Ser Phe
                425                 430                 435
His Ser Ile Lys Gln Ser Thr Ala Val
                440

<210> SEQ ID NO 3
<211> LENGTH: 375
<212> TYPE: PRT
<213> ORGANISM: Homo sapiens
<220> FEATURE:
<223> OTHER INFORMATION: amino acid sequence of human CRH-R1c
      gene: GenBank Accession No. U16273

<400> SEQUENCE: 3

Met Gly Gly His Pro Gln Leu Arg Leu Val Lys Ala Leu Leu Leu
                  5                  10                  15
Leu Gly Leu Asn Pro Val Ser Ala Ser Leu Gln Asp Gln His Cys
                 20                  25                  30
Glu Ser Leu Ser Leu Ala Ser Asn Ile Ser Asp Asn Gly Tyr Arg
                 35                  40                  45
Glu Cys Leu Ala Asn Gly Ser Trp Ala Ala Arg Val Asn Tyr Ser
                 50                  55                  60
Glu Cys Gln Glu Ile Leu Asn Glu Glu Lys Lys Ser Lys Val His
                 65                  70                  75
Tyr His Val Ala Val Ile Ile Asn Tyr Leu Gly His Cys Ile Ser
                 80                  85                  90
Leu Val Ala Leu Leu Val Ala Phe Val Leu Phe Leu Arg Leu Arg
                 95                 100                 105
Ser Ile Arg Cys Leu Arg Asn Ile Ile His Trp Asn Leu Ile Ser
                110                 115                 120
Ala Phe Ile Leu Arg Asn Ala Thr Trp Phe Val Val Gln Leu Thr
                125                 130                 135
Met Ser Pro Glu Val His Gln Ser Asn Val Gly Trp Cys Arg Leu
                140                 145                 150
Val Thr Ala Ala Tyr Asn Tyr Phe His Val Thr Asn Phe Phe Trp
                155                 160                 165
Met Phe Gly Glu Gly Cys Tyr Leu His Thr Ala Ile Val Leu Thr
                170                 175                 180
Tyr Ser Thr Asp Arg Leu Arg Lys Trp Met Phe Ile Cys Ile Gly
                185                 190                 195
Trp Gly Val Pro Phe Pro Ile Ile Val Ala Trp Ala Ile Gly Lys
                200                 205                 210
Leu Tyr Tyr Asp Asn Glu Lys Cys Trp Phe Gly Lys Arg Pro Gly
                215                 220                 225
Val Tyr Thr Asp Tyr Ile Tyr Gln Gly Pro Met Ile Leu Val Leu
                230                 235                 240
```

-continued

```
Leu Ile Asn Phe Ile Phe Leu Phe Asn Ile Val Arg Ile Leu Met
            245                 250                 255

Thr Lys Leu Arg Ala Ser Thr Thr Ser Glu Thr Ile Gln Tyr Arg
            260                 265                 270

Lys Ala Val Lys Ala Thr Leu Val Leu Leu Pro Leu Leu Gly Ile
            275                 280                 285

Thr Tyr Met Leu Phe Phe Val Asn Pro Gly Glu Asp Glu Val Ser
            290                 295                 300

Arg Val Val Phe Ile Tyr Phe Asn Ser Phe Leu Glu Ser Phe Gln
            305                 310                 315

Gly Phe Phe Val Ser Val Phe Tyr Cys Phe Leu Asn Ser Glu Val
            320                 325                 330

Arg Ser Ala Ile Arg Lys Arg Trp His Arg Trp Gln Asp Lys His
            335                 340                 345

Ser Ile Arg Ala Arg Val Ala Arg Ala Met Ser Ile Pro Thr Ser
            350                 355                 360

Pro Thr Arg Val Ser Phe His Ser Ile Lys Gln Ser Thr Ala Val
            365                 370                 375
```

<210> SEQ ID NO 4
<211> LENGTH: 401
<212> TYPE: PRT
<213> ORGANISM: Homo sapiens
<220> FEATURE:
<223> OTHER INFORMATION: amino acid sequence of human CRH-R1d
      gene: GenBank Accession No. AF180301

<400> SEQUENCE: 4

```
Met Gly Gly His Pro Gln Leu Arg Leu Val Lys Ala Leu Leu Leu
              5                  10                  15

Leu Gly Leu Asn Pro Val Ser Ala Ser Leu Gln Asp Gln His Cys
             20                  25                  30

Glu Ser Leu Ser Leu Ala Ser Asn Ile Ser Gly Leu Gln Cys Asn
             35                  40                  45

Ala Ser Val Asp Leu Ile Gly Thr Cys Trp Pro Arg Ser Pro Ala
             50                  55                  60

Gly Gln Leu Val Val Arg Pro Cys Pro Ala Phe Phe Tyr Gly Val
             65                  70                  75

Arg Tyr Asn Thr Thr Asn Asn Gly Tyr Arg Glu Cys Leu Ala Asn
             80                  85                  90

Gly Ser Trp Ala Ala Arg Val Asn Tyr Ser Glu Cys Gln Glu Ile
             95                 100                 105

Leu Asn Glu Glu Lys Lys Ser Lys Val His Tyr His Val Ala Val
            110                 115                 120

Ile Ile Asn Tyr Leu Gly His Cys Ile Ser Leu Val Ala Leu Leu
            125                 130                 135

Val Ala Phe Val Leu Phe Leu Arg Leu Arg Ser Ile Arg Cys Leu
            140                 145                 150

Arg Asn Ile Ile His Trp Asn Leu Ile Ser Ala Phe Ile Leu Arg
            155                 160                 165

Asn Ala Thr Trp Phe Val Val Gln Leu Thr Met Ser Pro Glu Val
            170                 175                 180

His Gln Ser Asn Val Gly Trp Cys Arg Leu Val Thr Ala Ala Tyr
            185                 190                 195

Asn Tyr Phe His Val Thr Asn Phe Phe Trp Met Phe Gly Glu Gly
            200                 205                 210
```

```
Cys Tyr Leu His Thr Ala Ile Val Leu Thr Tyr Ser Thr Asp Arg
            215                 220                 225

Leu Arg Lys Trp Met Phe Ile Cys Ile Gly Trp Gly Val Pro Phe
            230                 235                 240

Pro Ile Ile Val Ala Trp Ala Ile Gly Lys Leu Tyr Tyr Asp Asn
            245                 250                 255

Glu Lys Cys Trp Phe Gly Lys Arg Pro Gly Val Tyr Thr Asp Tyr
            260                 265                 270

Ile Tyr Gln Gly Pro Met Ile Leu Val Leu Leu Ile Asn Phe Ile
            275                 280                 285

Phe Leu Phe Asn Ile Val Arg Ile Leu Met Thr Lys Leu Arg Ala
            290                 295                 300

Ser Thr Thr Ser Glu Thr Ile Gln Tyr Arg Lys Ala Val Lys Ala
            305                 310                 315

Thr Leu Val Leu Leu Pro Leu Leu Gly Ile Thr Tyr Met Leu Phe
            320                 325                 330

Phe Val Asn Pro Gly Glu Asp Glu Val Ser Arg Val Val Phe Ile
            335                 340                 345

Tyr Phe Asn Ser Phe Leu Glu Ser Phe Gln Val Arg Ser Ala Ile
            350                 355                 360

Arg Lys Arg Trp His Arg Trp Gln Asp Lys His Ser Ile Arg Ala
            365                 370                 375

Arg Val Ala Arg Ala Met Ser Ile Pro Thr Ser Pro Thr Arg Val
            380                 385                 390

Ser Phe His Ser Ile Lys Gln Ser Thr Ala Val
            395                 400

<210> SEQ ID NO 5
<211> LENGTH: 194
<212> TYPE: PRT
<213> ORGANISM: Homo sapiens
<220> FEATURE:
<223> OTHER INFORMATION: amino acid sequence of human CRH-R1e1
      gene: GenBank Accession No. AF369651

<400> SEQUENCE: 5

Met Gly Gly His Pro Gln Leu Arg Leu Val Lys Ala Leu Leu Leu
              5                  10                  15

Leu Gly Leu Asn Pro Val Ser Ala Ser Leu Gln Asp Gln His Cys
             20                  25                  30

Glu Ser Leu Ser Leu Ala Ser Asn Ile Ser Glu Lys Lys Gln Gly
             35                  40                  45

Ala Leu Pro Cys Arg Ser His His Gln Leu Pro Gly Pro Leu Tyr
             50                  55                  60

Leu Pro Gly Gly Pro Pro Gly Gly Leu Cys Pro Leu Ser Ala Ala
             65                  70                  75

Gln Glu His Pro Val Glu Lys Lys Gln Gly Ala Leu Pro Cys Arg
             80                  85                  90

Ser His His Gln Leu Pro Gly Pro Leu Tyr Leu Pro Gly Gly Pro
             95                 100                 105

Pro Gly Gly Leu Cys Pro Leu Ser Ala Ala Gln Glu His Pro Val
            110                 115                 120

Pro Ala Lys His His Pro Leu Glu Pro His Leu Arg Leu His Pro
            125                 130                 135

Ala Gln Arg His Leu Val Arg Gly Pro Ala Asn His Glu Pro Arg
```

```
                140                 145                 150
Gly Pro Pro Glu Gln Arg Gly Leu Val Gln Val Gly Asp Ser Arg
                155                 160                 165

Leu Gln Leu Leu Pro Cys Asp Gln Leu Leu Asp Val Arg Arg
                170                 175                 180

Gly Leu Leu Pro Ala His Ser His Arg Ala His Leu Leu His
                185                 190

<210> SEQ ID NO 6
<211> LENGTH: 370
<212> TYPE: PRT
<213> ORGANISM: Homo sapiens
<220> FEATURE:
<223> OTHER INFORMATION: amino acid sequence of human CRH-R1f
      gene: GenBank Accession No. AF369652

<400> SEQUENCE: 6

Met Gly Gly His Pro Gln Leu Arg Leu Val Lys Ala Leu Leu Leu
                  5                  10                  15

Leu Gly Leu Asn Pro Val Ser Ala Ser Leu Gln Asp Gln His Cys
                 20                  25                  30

Glu Ser Leu Ser Leu Ala Ser Asn Ile Ser Gly Leu Gln Cys Asn
                 35                  40                  45

Ala Ser Val Asp Leu Ile Gly Thr Cys Trp Pro Arg Ser Pro Ala
                 50                  55                  60

Gly Gln Leu Val Val Arg Pro Cys Pro Ala Phe Phe Tyr Gly Val
                 65                  70                  75

Arg Tyr Asn Thr Thr Asn Asn Gly Tyr Arg Glu Cys Leu Ala Asn
                 80                  85                  90

Gly Ser Trp Ala Ala Arg Val Asn Tyr Ser Glu Cys Gln Glu Ile
                 95                 100                 105

Leu Asn Glu Glu Lys Lys Ser Lys Val His Tyr His Val Ala Val
                110                 115                 120

Ile Ile Asn Tyr Leu Gly His Cys Ile Ser Leu Val Ala Leu Leu
                125                 130                 135

Val Ala Phe Val Leu Phe Leu Arg Leu Arg Ser Ile Arg Cys Leu
                140                 145                 150

Arg Asn Ile Ile His Trp Asn Leu Ile Ser Ala Phe Ile Leu Arg
                155                 160                 165

Asn Ala Thr Trp Phe Val Val Gln Leu Thr Met Ser Pro Glu Val
                170                 175                 180

His Gln Ser Asn Val Gly Trp Cys Arg Leu Val Thr Ala Ala Tyr
                185                 190                 195

Asn Tyr Phe His Val Thr Asn Phe Phe Trp Met Phe Gly Glu Gly
                200                 205                 210

Cys Tyr Leu His Thr Ala Ile Val Leu Thr Tyr Ser Thr Asp Arg
                215                 220                 225

Leu Arg Lys Trp Met Phe Ile Cys Ile Gly Trp Gly Val Pro Phe
                230                 235                 240

Pro Ile Ile Val Ala Trp Ala Ile Gly Lys Leu Tyr Tyr Asp Asn
                245                 250                 255

Glu Lys Cys Trp Phe Gly Lys Arg Pro Gly Val Tyr Thr Asp Tyr
                260                 265                 270

Ile Tyr Gln Gly Pro Met Ile Leu Val Leu Leu Ile Asn Phe Ile
                275                 280                 285
```

-continued

```
Phe Leu Phe Asn Ile Val Arg Ile Leu Met Thr Lys Leu Arg Ala
            290                 295                 300

Ser Thr Thr Ser Glu Thr Ile Gln Tyr Arg Ala Ser Leu Cys Leu
            305                 310                 315

Cys Ser Thr Val Ser Ser Ile Val Arg Ser Val Leu Pro Ser Gly
            320                 325                 330

Arg Gly Gly Thr Gly Gly Arg Thr Ser Thr Arg Ser Val Pro Glu
            335                 340                 345

Trp Pro Val Pro Cys Pro Ser Pro Pro Gln Pro Val Ser Ala
            350                 355                 360

Phe Thr Ala Ser Ser Ser Pro Gln Gln Ser
            365                 370
```

<210> SEQ ID NO 7
<211> LENGTH: 341
<212> TYPE: PRT
<213> ORGANISM: Homo sapiens
<220> FEATURE:
<223> OTHER INFORMATION: amino acid sequence of human CRH-R1g
      gene: GenBank Accession No. AF369653

<400> SEQUENCE: 7

```
Met Gly Gly His Pro Gln Leu Arg Leu Val Lys Ala Leu Leu Leu
              5                  10                   15

Leu Gly Leu Asn Pro Val Ser Ala Ser Leu Gln Asp Gln His Cys
             20                   25                   30

Glu Ser Leu Ser Leu Ala Ser Asn Ile Ser Gly Leu Gln Cys Asn
             35                   40                   45

Ala Ser Val Asp Leu Ile Gly Thr Cys Trp Pro Arg Ser Pro Ala
             50                   55                   60

Gly Gln Leu Val Val Arg Pro Cys Pro Ala Phe Phe Tyr Gly Val
             65                   70                   75

Arg Tyr Asn Thr Thr Asn Asn Gly Tyr Arg Glu Cys Leu Ala Asn
             80                   85                   90

Gly Ser Trp Ala Ala Arg Val Asn Tyr Ser Glu Cys Gln Glu Ile
             95                  100                  105

Leu Asn Glu Glu Lys Lys Ser Lys Val His Tyr His Val Ala Val
            110                  115                  120

Ile Ile Asn Tyr Leu Gly His Cys Ile Ser Leu Val Ala Leu Leu
            125                  130                  135

Val Ala Phe Val Leu Phe Leu Arg Leu Arg Ser Ile Arg Cys Leu
            140                  145                  150

Arg Asn Ile Ile His Trp Asn Leu Ile Ser Ala Phe Ile Leu Arg
            155                  160                  165

Asn Ala Thr Trp Phe Val Val Gln Leu Thr Met Ser Pro Glu Val
            170                  175                  180

His Gln Ser Asn Val Gly Trp Cys Arg Leu Val Thr Ala Ala Tyr
            185                  190                  195

Asn Tyr Phe His Val Thr Asn Phe Phe Trp Met Phe Gly Glu Gly
            200                  205                  210

Cys Tyr Leu His Thr Ala Ile Val Leu Thr Tyr Ser Thr Asp Arg
            215                  220                  225

Leu Arg Lys Trp Met Phe Ile Cys Ile Gly Trp Gly Val Pro Phe
            230                  235                  240

Pro Ile Ile Val Ala Trp Ala Ile Gly Lys Leu Tyr Tyr Asp Asn
            245                  250                  255
```

```
Glu Lys Cys Trp Phe Gly Lys Arg Pro Gly Val Tyr Thr Asp Tyr
            260                 265                 270

Ile Tyr Phe Asn Ser Phe Leu Glu Ser Phe Gln Gly Phe Phe Val
            275                 280                 285

Ser Val Phe Tyr Cys Phe Leu Asn Ser Glu Val Arg Ser Ala Ile
            290                 295                 300

Arg Lys Arg Trp His Arg Trp Gln Asp Lys His Ser Ile Arg Ala
            305                 310                 315

Arg Val Ala Arg Ala Met Ser Ile Pro Thr Ser Pro Thr Arg Val
            320                 325                 330

Ser Phe His Ser Ile Lys Gln Ser Thr Ala Val
            335                 340

<210> SEQ ID NO 8
<211> LENGTH: 125
<212> TYPE: PRT
<213> ORGANISM: Homo sapiens
<220> FEATURE:
<223> OTHER INFORMATION: amino acid sequence of human CRH-R1h
      gene: GenBank Accession No. AF374231

<400> SEQUENCE: 8

Met Gly Gly His Pro Gln Leu Arg Leu Val Lys Ala Leu Leu Leu
              5                  10                  15

Leu Gly Leu Asn Pro Val Ser Ala Ser Leu Gln Asp Gln His Cys
             20                  25                  30

Glu Ser Leu Ser Leu Ala Ser Asn Ile Ser Gly Leu Gln Cys Asn
             35                  40                  45

Ala Ser Val Asp Leu Ile Gly Thr Cys Trp Pro Arg Ser Pro Ala
             50                  55                  60

Gly Gln Leu Val Val Arg Pro Cys Pro Ala Phe Phe Tyr Gly Val
             65                  70                  75

Arg Tyr Asn Thr Thr Asn Asn Gly Tyr Arg Glu Cys Leu Ala Asn
             80                  85                  90

Gly Ser Trp Ala Ala Arg Val Asn Tyr Ser Glu Cys Gln Glu Ile
             95                 100                 105

Leu Asn Glu Glu Glu Pro Gly Thr Gln Ala Gln Pro Gly Arg Ala
            110                 115                 120

His Arg Gly Gly Thr
            125

<210> SEQ ID NO 9
<211> LENGTH: 415
<212> TYPE: PRT
<213> ORGANISM: mouse
<220> FEATURE:
<223> OTHER INFORMATION: amino acid sequence of mouse CRH-R1 alpha
      gene: GenBank Accession No. NM_007762

<400> SEQUENCE: 9

Met Gly Gln Arg Pro Gln Leu Arg Leu Val Lys Ala Leu Leu Leu
              5                  10                  15

Leu Gly Leu Asn Pro Val Ser Thr Ser Leu Gln Asp Gln Gln Cys
             20                  25                  30

Glu Ser Leu Ser Leu Ala Ser Asn Val Ser Gly Leu Gln Cys Asn
             35                  40                  45

Ala Ser Val Asp Leu Ile Gly Thr Cys Trp Pro Arg Ser Pro Ala
             50                  55                  60
```

-continued

```
Gly Gln Leu Val Val Arg Pro Cys Pro Ala Phe Phe Tyr Gly Val
                 65                  70                  75
Arg Tyr Asn Thr Thr Asn Asn Gly Tyr Arg Glu Cys Leu Ala Asn
             80                  85                  90
Gly Ser Trp Ala Ala Arg Val Asn Tyr Ser Glu Cys Gln Glu Ile
         95                 100                 105
Leu Asn Glu Glu Lys Lys Ser Lys Val His Tyr His Ile Ala Val
            110                 115                 120
Ile Ile Asn Tyr Leu Gly His Cys Ile Ser Leu Val Ala Leu Leu
            125                 130                 135
Val Ala Phe Val Leu Phe Leu Arg Leu Arg Ser Ile Arg Cys Leu
            140                 145                 150
Arg Asn Ile Ile His Trp Asn Leu Ile Ser Ala Phe Ile Leu Arg
            155                 160                 165
Asn Ala Thr Trp Phe Val Val Gln Leu Thr Val Ser Pro Glu Val
            170                 175                 180
His Gln Ser Asn Val Ala Trp Cys Arg Leu Val Thr Ala Ala Tyr
            185                 190                 195
Asn Tyr Phe His Val Thr Asn Phe Phe Trp Met Phe Gly Glu Gly
            200                 205                 210
Cys Tyr Leu His Thr Ala Ile Val Leu Thr Tyr Ser Thr Asp Arg
            215                 220                 225
Leu Arg Lys Trp Met Phe Val Cys Ile Gly Trp Gly Val Pro Phe
            230                 235                 240
Pro Ile Ile Val Ala Trp Ala Ile Gly Lys Leu Tyr Tyr Asp Asn
            245                 250                 255
Glu Lys Cys Trp Phe Gly Lys Arg Pro Gly Val Tyr Thr Asp Tyr
            260                 265                 270
Ile Tyr Gln Gly Pro Met Ile Leu Val Leu Leu Ile Asn Phe Ile
            275                 280                 285
Phe Leu Phe Asn Ile Val Arg Ile Leu Met Thr Lys Leu Arg Ala
            290                 295                 300
Ser Thr Thr Ser Glu Thr Ile Gln Tyr Arg Lys Ala Val Lys Ala
            305                 310                 315
Thr Leu Val Leu Leu Pro Leu Leu Gly Ile Thr Tyr Met Leu Phe
            320                 325                 330
Phe Val Asn Pro Gly Glu Asp Glu Val Ser Arg Val Val Phe Ile
            335                 340                 345
Tyr Phe Asn Ser Phe Leu Glu Ser Phe Gln Gly Phe Phe Val Ser
            350                 355                 360
Val Phe Tyr Cys Phe Leu Asn Ser Glu Val Arg Ser Ala Ile Arg
            365                 370                 375
Lys Arg Trp Arg Arg Trp Gln Asp Lys His Ser Ile Arg Ala Arg
            380                 385                 390
Val Ala Arg Ala Met Ser Ile Pro Thr Ser Pro Thr Arg Val Ser
            395                 400                 405
Phe His Ser Ile Lys Gln Ser Thr Ala Val
            410                 415

<210> SEQ ID NO 10
<211> LENGTH: 375
<212> TYPE: PRT
<213> ORGANISM: mouse
<220> FEATURE:
```

-continued

<223> OTHER INFORMATION: amino acid sequence of mouse CRH-R1c
      gene: GenBank Accession No. AF369654

<400> SEQUENCE: 10

```
Met Gly Gln Arg Pro Gln Leu Arg Leu Val Lys Ala Leu Leu Leu
                 5                  10                  15

Leu Gly Leu Asn Pro Val Ser Thr Ser Leu Gln Asp Gln Gln Cys
                20                  25                  30

Glu Ser Leu Ser Leu Ala Ser Asn Val Ser Asp Asn Gly Tyr Arg
                35                  40                  45

Glu Cys Leu Ala Asn Gly Ser Trp Ala Ala Arg Val Asn Tyr Ser
                50                  55                  60

Glu Cys Gln Glu Ile Leu Asn Glu Glu Lys Lys Ser Lys Val His
                65                  70                  75

Tyr His Ile Ala Val Ile Ile Asn Tyr Leu Gly His Cys Ile Ser
                80                  85                  90

Leu Val Ala Leu Leu Val Ala Phe Val Leu Phe Leu Arg Leu Arg
                95                 100                 105

Ser Ile Arg Cys Leu Arg Asn Ile Ile His Trp Asn Leu Ile Ser
               110                 115                 120

Ala Phe Ile Leu Arg Asn Ala Thr Trp Phe Val Val Gln Leu Thr
               125                 130                 135

Val Ser Pro Glu Val His Gln Ser Asn Val Ala Trp Cys Arg Leu
               140                 145                 150

Val Thr Ala Ala Tyr Asn Tyr Phe His Val Thr Asn Phe Phe Trp
               155                 160                 165

Met Phe Gly Glu Gly Cys Tyr Leu His Thr Ala Ile Val Leu Thr
               170                 175                 180

Tyr Ser Thr Asp Arg Leu Arg Lys Trp Met Phe Val Cys Ile Gly
               185                 190                 195

Trp Gly Val Pro Phe Pro Ile Ile Val Ala Trp Ala Ile Gly Lys
               200                 205                 210

Leu Tyr Tyr Asp Asn Glu Lys Cys Trp Phe Gly Lys Arg Pro Gly
               215                 220                 225

Val Tyr Thr Asp Tyr Ile Tyr Gln Gly Pro Met Ile Leu Val Leu
               230                 235                 240

Leu Ile Asn Phe Ile Phe Leu Phe Asn Ile Val Arg Ile Leu Met
               245                 250                 255

Thr Lys Leu Arg Ala Ser Thr Thr Ser Glu Thr Ile Gln Tyr Arg
               260                 265                 270

Lys Ala Val Lys Ala Thr Leu Val Leu Leu Pro Leu Leu Gly Ile
               275                 280                 285

Thr Tyr Met Leu Phe Phe Val Asn Pro Gly Glu Asp Glu Val Ser
               290                 295                 300

Arg Val Val Phe Ile Tyr Phe Asn Ser Phe Leu Glu Ser Phe Gln
               305                 310                 315

Gly Phe Phe Val Ser Val Phe Tyr Cys Phe Leu Asn Ser Glu Val
               320                 325                 330

Arg Ser Ala Ile Arg Lys Arg Trp Arg Arg Trp Gln Asp Lys His
               335                 340                 345

Ser Ile Arg Ala Arg Val Ala Arg Ala Met Ser Ile Pro Thr Ser
               350                 355                 360

Pro Thr Arg Val Ser Phe His Ser Ile Lys Gln Ser Thr Ala Val
               365                 370                 375
```

<210> SEQ ID NO 11
<211> LENGTH: 139
<212> TYPE: PRT
<213> ORGANISM: mouse
<220> FEATURE:
<223> OTHER INFORMATION: amino acid sequence of mouse CRH-R1e1
      gene: GenBank Accession No. AF369655

<400> SEQUENCE: 11

Met Gly Gln Arg Pro Gln Leu Arg Leu Val Lys Ala Leu Leu Leu
                 5                  10                  15

Leu Gly Leu Asn Pro Val Ser Thr Ser Leu Gln Asp Gln Gln Cys
                20                  25                  30

Glu Ser Leu Ser Leu Ala Ser Asn Val Ser Glu Glu Glu Gln Ser
                35                  40                  45

Ala Leu Pro His Cys Arg His His Gln Leu Pro Gly Pro Leu His
                50                  55                  60

Leu Pro Gly Gly Pro Gly Gly Leu Cys Pro Leu Pro Ala Ala
                65                  70                  75

Gln Glu His Pro Val Pro Glu Glu His His Pro Leu Glu Pro His
                80                  85                  90

Leu Gly Phe His Pro Ala Gln Arg His Val Val Cys Gly Pro Ala
                95                  100                 105

His Arg Glu Pro Arg Gly Pro Pro Glu Gln Arg Gly Leu Val Gln
                110                 115                 120

Ala Gly Asp Ser Arg Leu Gln Leu Leu Pro Arg Asn Gln Leu Leu
                125                 130                 135

Leu Asp Val Arg

<210> SEQ ID NO 12
<211> LENGTH: 319
<212> TYPE: PRT
<213> ORGANISM: mouse
<220> FEATURE:
<223> OTHER INFORMATION: amino acid sequence of mouse CRH-R1f
      gene: GenBank Accession No. AF369656

<400> SEQUENCE: 12

Met Gly Gln Arg Pro Gln Leu Arg Leu Val Lys Ala Leu Leu Leu
                 5                  10                  15

Leu Gly Leu Asn Pro Val Ser Thr Ser Leu Gln Asp Gln Gln Cys
                20                  25                  30

Glu Ser Leu Ser Leu Ala Ser Asn Val Ser Gly Leu Gln Cys Asn
                35                  40                  45

Ala Ser Val Asp Leu Ile Gly Thr Cys Trp Pro Arg Ser Pro Ala
                50                  55                  60

Gly Gln Leu Val Val Arg Pro Cys Pro Ala Phe Phe Tyr Gly Val
                65                  70                  75

Arg Tyr Asn Thr Thr Asn Asn Gly Tyr Arg Glu Cys Leu Ala Asn
                80                  85                  90

Gly Ser Trp Ala Ala Arg Val Asn Tyr Ser Glu Cys Gln Glu Ile
                95                  100                 105

Leu Asn Glu Glu Lys Lys Ser Lys Val His Tyr His Ile Ala Val
                110                 115                 120

Ile Ile Asn Tyr Leu Gly His Cys Ile Ser Leu Val Ala Leu Leu
                125                 130                 135

```
Val Ala Phe Val Leu Phe Leu Arg Leu Arg Ser Ile Arg Cys Leu
                140                 145                 150

Arg Asn Ile Ile His Trp Asn Leu Ile Ser Ala Phe Ile Leu Arg
                155                 160                 165

Asn Ala Thr Trp Phe Val Val Gln Leu Thr Val Ser Pro Glu Val
                170                 175                 180

His Gln Ser Asn Val Ala Trp Cys Arg Leu Val Thr Ala Ala Tyr
                185                 190                 195

Asn Tyr Phe His Val Thr Asn Phe Phe Trp Met Phe Gly Glu Gly
                200                 205                 210

Cys Tyr Leu His Thr Ala Ile Val Leu Thr Tyr Ser Thr Asp Arg
                215                 220                 225

Leu Arg Lys Trp Met Phe Val Cys Ile Gly Trp Gly Val Pro Phe
                230                 235                 240

Pro Ile Ile Val Ala Trp Ala Ile Gly Lys Leu Tyr Tyr Asp Asn
                245                 250                 255

Glu Lys Cys Trp Phe Gly Lys Arg Pro Gly Val Tyr Thr Asp Tyr
                260                 265                 270

Ile Tyr Gln Gly Pro Met Ile Leu Val Leu Leu Ile Asn Phe Ile
                275                 280                 285

Phe Leu Phe Asn Ile Val Arg Ile Leu Met Thr Lys Leu Arg Ala
                290                 295                 300

Ser Thr Thr Ser Glu Thr Ile Gln Tyr Arg Ser Ser Cys Leu Cys
                305                 310                 315

Ser Ile Val Phe

<210> SEQ ID NO 13
<211> LENGTH: 309
<212> TYPE: PRT
<213> ORGANISM: mouse
<220> FEATURE:
<223> OTHER INFORMATION: amino acid sequence of mouse CRH-R1e2
      gene

<400> SEQUENCE: 13

Met Ser Leu Lys Lys Ser Lys Val His Tyr His Ile Ala Val Ile
                 5                  10                  15

Ile Asn Tyr Leu Gly His Cys Ile Ser Leu Val Ala Leu Leu Val
                20                  25                  30

Ala Phe Val Leu Phe Leu Arg Leu Arg Ser Ile Arg Cys Leu Arg
                35                  40                  45

Asn Ile Ile His Trp Asn Leu Ile Ser Ala Phe Ile Leu Arg Asn
                50                  55                  60

Ala Thr Trp Phe Val Val Gln Leu Thr Val Ser Pro Glu Val His
                65                  70                  75

Gln Ser Asn Val Ala Trp Cys Arg Leu Val Thr Ala Ala Tyr Asn
                80                  85                  90

Tyr Phe His Val Thr Asn Phe Phe Trp Met Phe Gly Glu Gly Cys
                95                  100                 105

Tyr Leu His Thr Ala Ile Val Leu Thr Tyr Ser Thr Asp Arg Leu
                110                 115                 120

Arg Lys Trp Met Phe Val Cys Ile Gly Trp Gly Val Pro Phe Pro
                125                 130                 135

Ile Ile Val Ala Trp Ala Ile Gly Lys Leu Tyr Tyr Asp Asn Glu
                140                 145                 150
```

```
Lys Cys Trp Phe Gly Lys Arg Pro Gly Val Tyr Thr Asp Tyr Ile
            155                 160                 165

Tyr Gln Gly Pro Met Ile Leu Val Leu Leu Ile Asn Phe Ile Phe
            170                 175                 180

Leu Phe Asn Ile Val Arg Ile Leu Met Thr Lys Leu Arg Ala Ser
            185                 190                 195

Thr Thr Ser Glu Thr Ile Gln Tyr Arg Lys Ala Val Lys Ala Thr
            200                 205                 210

Leu Val Leu Leu Pro Leu Leu Gly Ile Thr Tyr Met Leu Phe Phe
            215                 220                 225

Val Asn Pro Gly Glu Asp Glu Val Ser Arg Val Val Phe Ile Tyr
            230                 235                 240

Phe Asn Ser Phe Leu Glu Ser Phe Gln Gly Phe Phe Val Ser Val
            245                 250                 255

Phe Tyr Cys Phe Leu Asn Ser Glu Val Arg Ser Ala Ile Arg Lys
            260                 265                 270

Arg Trp Arg Arg Trp Gln Asp Lys His Ser Ile Arg Ala Arg Val
            275                 280                 285

Ala Arg Ala Met Ser Ile Pro Thr Ser Pro Thr Arg Val Ser Phe
            290                 295                 300

His Ser Ile Lys Gln Ser Thr Ala Val
            305

<210> SEQ ID NO 14
<211> LENGTH: 240
<212> TYPE: PRT
<213> ORGANISM: Homo sapiens
<220> FEATURE:
<223> OTHER INFORMATION: amino acid sequence of human CRH-R1e2
      gene

<400> SEQUENCE: 14

Met Ser Pro Glu Val His Gln Ser Asn Val Gly Trp Cys Arg Leu
              5                  10                  15

Val Thr Ala Ala Tyr Asn Tyr Phe His Val Thr Asn Phe Phe Trp
             20                  25                  30

Met Phe Gly Glu Gly Cys Tyr Leu His Thr Ala Ile Val Leu Thr
             35                  40                  45

Tyr Ser Thr Asp Arg Leu Arg Lys Trp Met Phe Ile Cys Ile Gly
             50                  55                  60

Trp Gly Val Pro Phe Pro Ile Ile Val Ala Trp Ala Ile Gly Lys
             65                  70                  75

Leu Tyr Tyr Asp Asn Glu Lys Cys Trp Phe Gly Lys Arg Pro Gly
             80                  85                  90

Val Tyr Thr Asp Tyr Ile Tyr Gln Gly Pro Met Ile Leu Val Leu
             95                 100                 105

Leu Ile Asn Phe Ile Phe Leu Phe Asn Ile Val Arg Ile Leu Met
            110                 115                 120

Thr Lys Leu Arg Ala Ser Thr Thr Ser Glu Thr Ile Gln Tyr Arg
            125                 130                 135

Lys Ala Val Lys Ala Thr Leu Val Leu Leu Pro Leu Leu Gly Ile
            140                 145                 150

Thr Tyr Met Leu Phe Phe Val Asn Pro Gly Glu Asp Glu Val Ser
            155                 160                 165

Arg Val Val Phe Ile Tyr Phe Asn Ser Phe Leu Glu Ser Phe Gln
            170                 175                 180
```

```
Gly Phe Phe Val Ser Val Phe Tyr Cys Phe Leu Asn Ser Glu Val
            185                 190                 195

Arg Ser Ala Ile Arg Lys Arg Trp His Arg Trp Gln Asp Lys His
            200                 205                 210

Ser Ile Arg Ala Arg Val Ala Arg Ala Met Ser Ile Pro Thr Ser
            215                 220                 225

Pro Thr Arg Val Ser Phe His Ser Ile Lys Gln Ser Thr Ala Val
            230                 235                 240

<210> SEQ ID NO 15
<211> LENGTH: 21
<212> TYPE: DNA
<213> ORGANISM: artificial sequence
<220> FEATURE:
<223> OTHER INFORMATION: forward primer P110

<400> SEQUENCE: 15
tccgtctcgt caaggcccTT c                                        21

<210> SEQ ID NO 16
<211> LENGTH: 22
<212> TYPE: DNA
<213> ORGANISM: artificial sequence
<220> FEATURE:
<223> OTHER INFORMATION: reverse primer P111

<400> SEQUENCE: 16
ggctcatggt tagctggacc ac                                       22

<210> SEQ ID NO 17
<211> LENGTH: 22
<212> TYPE: DNA
<213> ORGANISM: artificial sequence
<220> FEATURE:
<223> OTHER INFORMATION: forward primer P112

<400> SEQUENCE: 17
tgtccctggc cagcaacatc tc                                       22

<210> SEQ ID NO 18
<211> LENGTH: 23
<212> TYPE: DNA
<213> ORGANISM: artificial sequence
<220> FEATURE:
<223> OTHER INFORMATION: reverse primer P113

<400> SEQUENCE: 18
agtggatgat gtttcgcagg cac                                      23

<210> SEQ ID NO 19
<211> LENGTH: 23
<212> TYPE: DNA
<213> ORGANISM: artificial sequence
<220> FEATURE:
<223> OTHER INFORMATION: forward primer P114

<400> SEQUENCE: 19
ccattgggaa gctgtactac gac                                      23

<210> SEQ ID NO 20
<211> LENGTH: 24
<212> TYPE: DNA
<213> ORGANISM: artificial sequence
<220> FEATURE:
```

```
<223> OTHER INFORMATION: reverse primer P115

<400> SEQUENCE: 20
gcttgatgct gtgaaagctg acac                                          24

<210> SEQ ID NO 21
<211> LENGTH: 23
<212> TYPE: DNA
<213> ORGANISM: artificial sequence
<220> FEATURE:
<223> OTHER INFORMATION: forward primer P116

<400> SEQUENCE: 21
gggtgtacac cgactacatc tac                                           23

<210> SEQ ID NO 22
<211> LENGTH: 22
<212> TYPE: DNA
<213> ORGANISM: artificial sequence
<220> FEATURE:
<223> OTHER INFORMATION: reverse primer P117

<400> SEQUENCE: 22
tcttccggat ggcagaacgg ac                                            22

<210> SEQ ID NO 23
<211> LENGTH: 21
<212> TYPE: DNA
<213> ORGANISM: artificial sequence
<220> FEATURE:
<223> OTHER INFORMATION: forward primer P156

<400> SEQUENCE: 23
tccggctcgt gaaggccctt c                                             21

<210> SEQ ID NO 24
<211> LENGTH: 21
<212> TYPE: DNA
<213> ORGANISM: artificial sequence
<220> FEATURE:
<223> OTHER INFORMATION: reverse primer P157

<400> SEQUENCE: 24
gctcagggtg agctggacca c                                             21

<210> SEQ ID NO 25
<211> LENGTH: 22
<212> TYPE: DNA
<213> ORGANISM: artificial sequence
<220> FEATURE:
<223> OTHER INFORMATION: forward primer P158

<400> SEQUENCE: 25
tgtccctggc cagcaatgtc tc                                            22

<210> SEQ ID NO 26
<211> LENGTH: 23
<212> TYPE: DNA
<213> ORGANISM: artificial sequence
<220> FEATURE:
<223> OTHER INFORMATION: reverse primer P159

<400> SEQUENCE: 26
agtggatgat gttcctcagg cac                                           23
```

```
<210> SEQ ID NO 27
<211> LENGTH: 23
<212> TYPE: DNA
<213> ORGANISM: artificial sequence
<220> FEATURE:
<223> OTHER INFORMATION: forward primer P160

<400> SEQUENCE: 27
ccattgggaa actttactac gac                                      23

<210> SEQ ID NO 28
<211> LENGTH: 23
<212> TYPE: DNA
<213> ORGANISM: artificial sequence
<220> FEATURE:
<223> OTHER INFORMATION: reverse primer P161

<400> SEQUENCE: 28
cttgatgctg tggaagctga ctc                                      23

<210> SEQ ID NO 29
<211> LENGTH: 24
<212> TYPE: DNA
<213> ORGANISM: artificial sequence
<220> FEATURE:
<223> OTHER INFORMATION: forward primer P162

<400> SEQUENCE: 29
aaaagtgctg gtttggcaaa cgtc                                     24

<210> SEQ ID NO 30
<211> LENGTH: 21
<212> TYPE: DNA
<213> ORGANISM: artificial sequence
<220> FEATURE:
<223> OTHER INFORMATION: reverse primer P163

<400> SEQUENCE: 30
cttccggatg gcagagcgga c                                        21

<210> SEQ ID NO 31
<211> LENGTH: 139
<212> TYPE: PRT
<213> ORGANISM: hamster
<220> FEATURE:
<223> OTHER INFORMATION: amino acid sequence of hamster CRH-R1e
      gene: GenBank Accession No. AF387669

<400> SEQUENCE: 31

Met Gly Gln Arg Pro Gln Leu Pro Leu Val Lys Ala Leu Leu Leu
                 5                  10                  15

Leu Gly Leu Asn Pro Val Ser Thr Thr Leu Gln Asp Gln Arg Cys
                20                  25                  30

Glu Ser Leu Ser Leu Ala Ser Asn Val Ser Glu Glu Lys Gln Ser
                35                  40                  45

Ala Leu Pro His Cys Arg His His Gln Leu Pro Gly Pro Leu His
                50                  55                  60

Leu Pro Gly Ser Pro Leu Gly Gly Leu Cys Pro Leu Ser Ala Ser
                65                  70                  75

Gln Glu His Pro Val Pro Glu Glu His Pro Leu Glu Pro His
                80                  85                  90

Leu Gly Phe His Pro Ala Gln Cys His Val Val Cys Gly Pro Ala
                95                 100                 105
```

-continued

```
His His Glu Pro Arg Gly Pro Pro Glu Gln Cys Gly Met Val Gln
            110                 115                 120

Val Gly Asp Ser Cys Leu Gln Leu Phe Pro Arg His Gln Leu Leu
            125                 130                 135

Leu Asp Val Trp

<210> SEQ ID NO 32
<211> LENGTH: 320
<212> TYPE: PRT
<213> ORGANISM: hamster
<220> FEATURE:
<223> OTHER INFORMATION: amino acid sequence of hamster CRH-R1f
      gene: GenBank Accession No. AF387671

<400> SEQUENCE: 32

Met Gly Gln Arg Pro Gln Leu Pro Leu Val Lys Ala Leu Leu Leu
              5                  10                  15

Leu Gly Leu Asn Pro Val Ser Thr Thr Leu Gln Asp Gln Arg Cys
             20                  25                  30

Glu Ser Leu Ser Leu Ala Ser Asn Val Ser Gly Pro Gln Cys Asn
             35                  40                  45

Ala Ser Val Asp Leu Ile Gly Thr Cys Trp Pro Arg Ser Pro Ala
             50                  55                  60

Gly Gln Leu Val Val Arg Pro Cys Pro Ala Phe Phe Tyr Gly Val
             65                  70                  75

Arg Tyr Asn Thr Thr Asn Asn Gly Tyr Arg Glu Cys Leu Ala Asn
             80                  85                  90

Gly Ser Trp Ala Ala Arg Val Asn Tyr Ser Glu Cys Gln Glu Ile
             95                 100                 105

Leu Asn Glu Glu Lys Lys Ser Lys Val His Tyr His Ile Ala Val
            110                 115                 120

Ile Ile Asn Tyr Leu Gly His Cys Ile Ser Leu Val Ala Leu Leu
            125                 130                 135

Val Ala Phe Val Leu Phe Leu Arg Leu Arg Ser Ile Arg Cys Leu
            140                 145                 150

Arg Asn Ile Ile His Trp Asn Leu Ile Ser Ala Phe Ile Leu Arg
            155                 160                 165

Asn Ala Thr Trp Phe Val Val Gln Leu Thr Met Ser Pro Glu Val
            170                 175                 180

His Gln Ser Asn Val Gly Trp Cys Arg Leu Val Thr Ala Ala Tyr
            185                 190                 195

Asn Tyr Phe His Val Thr Asn Phe Phe Trp Met Phe Gly Glu Gly
            200                 205                 210

Cys Tyr Leu His Thr Ala Ile Val Pro Thr Tyr Ser Thr Asp Arg
            215                 220                 225

Leu Arg Lys Trp Met Phe Val Cys Ile Gly Trp Gly Val Pro Phe
            230                 235                 240

Pro Ile Ile Val Ala Trp Ala Ile Gly Lys Leu Tyr Tyr Asp Asn
            245                 250                 255

Glu Lys Cys Trp Phe Gly Lys Arg Pro Gly Val Tyr Thr Asp Tyr
            260                 265                 270

Ile Tyr Gln Gly Pro Met Ile Leu Val Leu Leu Ile Asn Phe Ile
            275                 280                 285

Phe Leu Phe Asn Ile Val Arg Ile Leu Met Thr Lys Leu Arg Ala
            290                 295                 300
```

```
Ser Thr Thr Ser Glu Thr Ile Gln Tyr Arg Thr Ser Leu Cys Leu
            305                 310                 315

Cys Ser Thr Val Phe
            320

<210> SEQ ID NO 33
<211> LENGTH: 114
<212> TYPE: PRT
<213> ORGANISM: hamster
<220> FEATURE:
<223> OTHER INFORMATION: amino acid sequence of hamster CRH-R1h
      gene: GenBank Accession No. AF387667

<400> SEQUENCE: 33

Met Gly Gln Arg Pro Gln Leu Pro Leu Val Lys Ala Leu Leu Leu
              5                  10                  15

Leu Gly Leu Asn Pro Val Ser Thr Thr Leu Gln Asp Gln Arg Cys
             20                  25                  30

Glu Ser Leu Ser Leu Ala Ser Asn Val Ser Gly Pro Gln Cys Asn
             35                  40                  45

Ala Ser Val Asp Leu Ile Gly Thr Cys Trp Pro Arg Ser Pro Ala
             50                  55                  60

Gly Gln Leu Val Val Arg Pro Cys Pro Ala Phe Phe Tyr Gly Val
             65                  70                  75

Arg Tyr Asn Thr Thr Asn Asn Gly Tyr Arg Glu Cys Leu Ala Asn
             80                  85                  90

Gly Ser Trp Ala Ala Arg Val Asn Tyr Ser Glu Cys Gln Glu Ile
             95                 100                 105

Leu Asn Glu Glu Glu Trp Leu Arg Met
            110

<210> SEQ ID NO 34
<211> LENGTH: 172
<212> TYPE: PRT
<213> ORGANISM: hamster
<220> FEATURE:
<223> OTHER INFORMATION: amino acid sequence of hamster CRH-R1j
      gene: GenBank Accession No. AF387668

<400> SEQUENCE: 34

Met Gly Gln Arg Pro Gln Leu Pro Leu Val Lys Ala Leu Leu Leu
              5                  10                  15

Leu Gly Leu Asn Pro Val Ser Thr Thr Leu Gln Asp Gln Arg Cys
             20                  25                  30

Glu Ser Leu Ser Leu Ala Ser Asn Val Ser Gly Pro Gln Cys Asn
             35                  40                  45

Ala Ser Val Asp Leu Ile Gly Thr Cys Trp Pro Arg Ser Pro Ala
             50                  55                  60

Gly Gln Leu Val Val Arg Pro Cys Pro Ala Phe Phe Tyr Gly Val
             65                  70                  75

Arg Tyr Asn Thr Thr Asn Asn Gly Tyr Arg Glu Cys Leu Ala Asn
             80                  85                  90

Gly Ser Trp Ala Ala Arg Val Asn Tyr Ser Glu Cys Gln Glu Ile
             95                 100                 105

Leu Asn Glu Glu Glu His Pro Val Pro Glu His His Pro Leu
            110                 115                 120

Glu Pro His Leu Gly Phe His Pro Ala Gln Cys His Val Cys
            125                 130                 135
```

```
Gly Pro Ala His His Glu Pro Arg Gly Pro Pro Glu Gln Cys Gly
                140                 145                 150

Met Val Gln Val Gly Asp Ser Cys Leu Gln Leu Phe Pro Arg His
                155                 160                 165

Gln Leu Leu Leu Asp Val Trp
                170
```

<210> SEQ ID NO 35
<211> LENGTH: 339
<212> TYPE: PRT
<213> ORGANISM: hamster
<220> FEATURE:
<223> OTHER INFORMATION: amino acid sequence of hamster CRH-R1k
      gene: GenBank Accession No. AF387670

<400> SEQUENCE: 35

```
Met Gly Gln Arg Pro Gln Leu Pro Leu Val Lys Ala Leu Leu Leu
                  5                  10                  15

Leu Gly Leu Asn Pro Val Ser Thr Thr Leu Gln Asp Gln Arg Cys
                 20                  25                  30

Glu Ser Leu Ser Leu Ala Ser Asn Val Ser Gly Pro Gln Cys Asn
                 35                  40                  45

Ala Ser Val Asp Leu Ile Gly Thr Cys Trp Pro Arg Ser Pro Ala
                 50                  55                  60

Gly Gln Leu Val Val Arg Pro Cys Pro Ala Phe Phe Tyr Gly Val
                 65                  70                  75

Arg Tyr Asn Thr Thr Asn Asn Gly Tyr Arg Glu Cys Leu Ala Asn
                 80                  85                  90

Gly Ser Trp Ala Ala Arg Val Asn Tyr Ser Glu Cys Gln Glu Ile
                 95                 100                 105

Leu Asn Glu Glu Lys Lys Ser Lys Val His Tyr His Ile Ala Val
                110                 115                 120

Ile Ile Asn Tyr Leu Gly His Cys Ile Ser Leu Val Ala Leu Leu
                125                 130                 135

Val Ala Phe Val Leu Phe Leu Arg Leu Arg Ser Ile Arg Cys Leu
                140                 145                 150

Arg Asn Ile Ile His Trp Asn Leu Ile Ser Ala Phe Ile Leu Arg
                155                 160                 165

Asn Ala Thr Trp Phe Val Val Gln Leu Thr Met Ser Pro Glu Val
                170                 175                 180

His Gln Ser Asn Val Gly Trp Cys Arg Leu Val Thr Ala Ala Tyr
                185                 190                 195

Asn Tyr Phe His Val Thr Asn Phe Phe Trp Met Phe Gly Glu Gly
                200                 205                 210

Cys Tyr Leu His Thr Ala Ile Val Pro Thr Tyr Ser Thr Asp Arg
                215                 220                 225

Leu Arg Lys Trp Met Phe Val Cys Ile Gly Trp Gly Val Pro Phe
                230                 235                 240

Pro Ile Ile Val Ala Trp Ala Ile Gly Lys Leu Tyr Tyr Asp Asn
                245                 250                 255

Glu Lys Cys Trp Phe Gly Lys Arg Pro Gly Val Tyr Thr Asp Tyr
                260                 265                 270

Ile Tyr Gln Gly Pro Met Ile Leu Val Leu Leu Glu Gly Cys Glu
                275                 280                 285

Gly His Ser Gly Ala Ala Ala Pro Pro Gly His His Leu His Val
                290                 295                 300
```

-continued

```
Ile Leu Cys Gln Pro Trp Gly Gly Arg Gly Leu Gln Gly Arg Leu
            305                 310                 315

His Leu Gln Leu Phe Pro Gly Val Leu Pro Gly Leu Leu Cys
            320                 325                 330

Val Cys Val Leu Leu Phe Ser Glu Gln
            335
```

<210> SEQ ID NO 36
<211> LENGTH: 356
<212> TYPE: PRT
<213> ORGANISM: hamster
<220> FEATURE:
<223> OTHER INFORMATION: amino acid sequence of hamster CRH-R1m
      gene: GenBank Accession No. AF387672

<400> SEQUENCE: 36

```
Met Gly Gln Arg Pro Gln Leu Pro Leu Val Lys Ala Leu Leu Leu
              5                  10                  15

Leu Gly Leu Asn Pro Val Ser Thr Thr Leu Gln Asp Gln Arg Cys
             20                  25                  30

Glu Ser Leu Ser Leu Ala Ser Asn Val Ser Gly Pro Gln Cys Asn
             35                  40                  45

Ala Ser Val Asp Leu Ile Gly Thr Cys Trp Pro Arg Ser Pro Ala
             50                  55                  60

Gly Gln Leu Val Val Arg Pro Cys Pro Ala Phe Phe Tyr Gly Val
             65                  70                  75

Arg Tyr Asn Thr Thr Asn Asn Gly Tyr Arg Glu Cys Leu Ala Asn
             80                  85                  90

Gly Ser Trp Ala Ala Arg Val Asn Tyr Ser Glu Cys Gln Glu Ile
             95                 100                 105

Leu Asn Glu Glu Lys Lys Ser Lys Val His Tyr His Ile Ala Val
            110                 115                 120

Ile Ile Asn Tyr Leu Gly His Cys Ile Ser Leu Val Ala Leu Leu
            125                 130                 135

Val Ala Phe Val Leu Phe Leu Arg Leu Arg Ser Ile Arg Cys Leu
            140                 145                 150

Arg Asn Ile Ile His Trp Asn Leu Ile Ser Ala Phe Ile Leu Arg
            155                 160                 165

Asn Ala Thr Trp Phe Val Val Gln Leu Thr Met Ser Pro Glu Val
            170                 175                 180

His Gln Ser Asn Val Gly Trp Cys Arg Leu Val Thr Ala Ala Tyr
            185                 190                 195

Asn Tyr Phe His Val Thr Asn Phe Phe Trp Met Phe Gly Glu Gly
            200                 205                 210

Cys Tyr Leu His Thr Ala Ile Val Pro Thr Tyr Ser Thr Asp Arg
            215                 220                 225

Leu Arg Lys Trp Met Phe Val Cys Ile Gly Trp Gly Val Pro Phe
            230                 235                 240

Pro Ile Ile Val Ala Trp Ala Ile Gly Lys Leu Tyr Tyr Asp Asn
            245                 250                 255

Glu Lys Cys Trp Phe Gly Lys Arg Pro Gly Val Tyr Thr Asp Tyr
            260                 265                 270

Ile Tyr Gln Gly Pro Met Ile Leu Val Leu Leu Ile Asn Phe Ile
            275                 280                 285

Phe Leu Phe Asn Ile Val Arg Ile Leu Met Thr Lys Leu Arg Ala
```

-continued

```
                290                 295                 300
Ser Thr Thr Ser Glu Thr Ile Gln Tyr Arg Ser Ala Leu Pro Ser
            305                 310                 315
Gly Arg Gly Gly Ile Gly Gly Arg Ile Ser Thr Arg Ser Glu Pro
            320                 325                 330
Glu Trp Pro Ala Pro Cys Pro Ser Pro Pro Pro Pro Glu Ser
            335                 340                 345
Ala Ser Thr Ala Ser Ser Lys Pro Gln Gln Cys
            350                 355

<210> SEQ ID NO 37
<211> LENGTH: 327
<212> TYPE: PRT
<213> ORGANISM: hamster
<220> FEATURE:
<223> OTHER INFORMATION: amino acid sequence of hamster CRH-R1n
      gene: GenBank Accession No. AF387673

<400> SEQUENCE: 37

Met Gly Gln Arg Pro Gln Leu Pro Leu Val Lys Ala Leu Leu Leu
                  5                  10                  15
Leu Gly Leu Asn Pro Val Ser Thr Thr Leu Gln Asp Gln Arg Cys
                 20                  25                  30
Glu Ser Leu Ser Leu Ala Ser Asn Val Ser Gly Pro Gln Cys Asn
                 35                  40                  45
Ala Ser Val Asp Leu Ile Gly Thr Cys Trp Pro Arg Ser Pro Ala
                 50                  55                  60
Gly Gln Leu Val Val Arg Pro Cys Pro Ala Phe Phe Tyr Gly Val
                 65                  70                  75
Arg Tyr Asn Thr Thr Asn Asn Gly Tyr Arg Glu Cys Leu Ala Asn
                 80                  85                  90
Gly Ser Trp Ala Ala Arg Val Asn Tyr Ser Glu Cys Gln Glu Ile
                 95                 100                 105
Leu Asn Glu Glu Lys Lys Ser Lys Val His Tyr His Ile Ala Val
                110                 115                 120
Ile Ile Asn Tyr Leu Gly His Cys Ile Ser Leu Val Ala Leu Leu
                125                 130                 135
Val Ala Phe Val Leu Phe Leu Arg Leu Arg Ser Ile Arg Cys Leu
                140                 145                 150
Arg Asn Ile Ile His Trp Asn Leu Ile Ser Ala Phe Ile Leu Arg
                155                 160                 165
Asn Ala Thr Trp Phe Val Val Gln Leu Thr Met Ser Pro Glu Val
                170                 175                 180
His Gln Ser Asn Val Gly Trp Cys Arg Leu Val Thr Ala Ala Tyr
                185                 190                 195
Asn Tyr Phe His Val Thr Asn Phe Phe Trp Met Phe Gly Glu Gly
                200                 205                 210
Cys Tyr Leu His Thr Ala Ile Val Pro Thr Tyr Ser Thr Asp Arg
                215                 220                 225
Leu Arg Lys Trp Met Phe Val Cys Ile Gly Trp Gly Val Pro Phe
                230                 235                 240
Pro Ile Ile Val Ala Trp Ala Ile Gly Lys Leu Tyr Tyr Asp Asn
                245                 250                 255
Glu Lys Cys Trp Phe Gly Lys Arg Pro Gly Val Tyr Thr Asp Tyr
                260                 265                 270
```

```
Ile Tyr Gln Gly Pro Met Ile Leu Val Leu Leu Val Arg Ser Ala
            275                 280                 285

Ile Arg Lys Arg Trp His Arg Trp Gln Asp Lys His Ser Ile Arg
            290                 295                 300

Ala Arg Val Ala Arg Ala Met Ser Ile Pro Thr Ser Pro Thr Arg
            305                 310                 315

Val Ser Phe His Ser Ile Lys Gln Ala Thr Ala Val
            320                 325
```

<210> SEQ ID NO 38
<211> LENGTH: 27
<212> TYPE: DNA
<213> ORGANISM: artificial sequence
<220> FEATURE:
<223> OTHER INFORMATION: forward primer E3

<400> SEQUENCE: 38
aaaagcttag gacccgggca ttcagga                                   27

<210> SEQ ID NO 39
<211> LENGTH: 32
<212> TYPE: DNA
<213> ORGANISM: artificial sequence
<220> FEATURE:
<223> OTHER INFORMATION: reverse primer E9

<400> SEQUENCE: 39
gaaggagttg aagtagatgt agtcggtgta ca                             32

<210> SEQ ID NO 40
<211> LENGTH: 28
<212> TYPE: DNA
<213> ORGANISM: artificial sequence
<220> FEATURE:
<223> OTHER INFORMATION: reverse primer E11

<400> SEQUENCE: 40
aagaattctc agactgctgt ggactgct                                  28

<210> SEQ ID NO 41
<211> LENGTH: 22
<212> TYPE: DNA
<213> ORGANISM: artificial sequence
<220> FEATURE:
<223> OTHER INFORMATION: forward primer E12

<400> SEQUENCE: 41
catctacttc aactccttcc tg                                        22

<210> SEQ ID NO 42
<211> LENGTH: 30
<212> TYPE: DNA
<213> ORGANISM: artificial sequence
<220> FEATURE:
<223> OTHER INFORMATION: forward primer E16

<400> SEQUENCE: 42
cattcagtac agggcttctt tgtgtctgtg                                30

<210> SEQ ID NO 43
<211> LENGTH: 26
<212> TYPE: DNA
<213> ORGANISM: artificial sequence
<220> FEATURE:
<223> OTHER INFORMATION: reverse primer E17

```
<400> SEQUENCE: 43
aagaattctc atccccccag ccacag                                      26

<210> SEQ ID NO 44
<211> LENGTH: 30
<212> TYPE: DNA
<213> ORGANISM: artificial sequence
<220> FEATURE:
<223> OTHER INFORMATION: reverse primer E18

<400> SEQUENCE: 44
acaaagaagc cctgtactga atggtctcag                                  30

<210> SEQ ID NO 45
<211> LENGTH: 30
<212> TYPE: DNA
<213> ORGANISM: artificial sequence
<220> FEATURE:
<223> OTHER INFORMATION: reverse primer E19

<400> SEQUENCE: 45
aagaattctt tgtcccacca cggtgtgctc                                  30

<210> SEQ ID NO 46
<211> LENGTH: 20
<212> TYPE: DNA
<213> ORGANISM: artificial sequence
<220> FEATURE:
<223> OTHER INFORMATION: reverse primer E24

<400> SEQUENCE: 46
ctcctcattg aggatctcct                                             20

<210> SEQ ID NO 47
<211> LENGTH: 32
<212> TYPE: DNA
<213> ORGANISM: artificial sequence
<220> FEATURE:
<223> OTHER INFORMATION: forward primer E25

<400> SEQUENCE: 47
cttgcttttt ttgagatgtt gctggccagg ga                               32

<210> SEQ ID NO 48
<211> LENGTH: 31
<212> TYPE: DNA
<213> ORGANISM: artificial sequence
<220> FEATURE:
<223> OTHER INFORMATION: forward primer E27

<400> SEQUENCE: 48
ggtagtgcac cttgcttttt ttctctcccc a                                31

<210> SEQ ID NO 49
<211> LENGTH: 33
<212> TYPE: DNA
<213> ORGANISM: artificial sequence
<220> FEATURE:
<223> OTHER INFORMATION: reverse primer E28

<400> SEQUENCE: 49
tggtagtgca ccttgctttt tttgagatgt tgc                              33
```

VARIANTS OF CORTICOTROPIN RELEASING HORMONE RECEPTOR TYPE 1 AND USES THEREOF

CROSS-REFERENCE TO RELATED APPLICATION

This non-provisional patent application claims benefit of provisional patent application U.S. Ser. No. 60/322,195, filed Sep. 14, 2001, now abandoned.

FEDERAL FUNDING LEGEND

This invention was produced in part using funds obtained through grant IBN-049087 from the National Science Foundation. Consequently, the federal government has certain rights in this invention.

BACKGROUND OF THE INVENTION

1. Field of the Invention

The present invention relates generally to the field of biochemical endocrinology of corticotropin releasing hormone receptors. More specifically, the present invention relates to the identification of alternative splicing variants of human and mouse corticotropin releasing hormone receptor-1.

2. Description of the Related Art

Corticotropin releasing hormone (CRH, also known a s corticotropin releasing factor or CRF) is the most proximal element of the hypothalamic-pituitary-adrenal (HPA) axis that coordinates the complex array of behavioral, autonomic, endocrine and immune responses to stress. The peptide signal is translated into phenotypic effects through interaction with G protein-coupled, membrane-bound CRH receptors (1). Two subtypes of receptors, Type 1 (CRH-R1) and Type 2 (CRH-R2), have been characterized in humans (2, 3), rats (4–6), mice (7–9) and *Xenopus* (10). Most recently a third subtype, CRH-R3, has been identified in catfish (11).

CRH-R1 is a protein with 98% sequence homology among different mammalian species and approximately 30% homology with receptors for the gut-brain family of neuropeptides (1, 12, 13). The human CRH-R1 gene contains 14 exons (14). Four alternatively spliced CRH-R1 transcripts have been identified in humans. These are CRH-R1α, in which exon 6 is spliced out to generate a 13-exon transcript that produces a 415-amino acid protein (2); CRH-R1β, which contains all 14 exons to produce a 444-amino acid protein (2); a CRH-R1c isoform, where exons 3 and 6 are spliced out to generate a 12-exon transcript producing a 375-amino acid protein (15); and an CRH-R1d isoform, where exons 6 and 13 are spliced out to produce a 401-amino acid protein (16).

CRH-R1 isoforms have different affinity for receptor ligands, resulting in differences in coupling of the isoforms to cAMP production signaling. The major ligand-binding determinant of mammalian CRH-R1 has been mapped to its first extracellular domain (17). This domain is encoded by exons 1–4 of CRH-R1. Exon 3 contains two regions that are critical for high-affinity ligand binding; thus, mutations in this region abolish CRH binding (18). The CRH-R1c isoform, which lacks exon 3, should therefore have a decreased CRH binding capacity. A 29 amino acid insert corresponding to exon 6 of CRH-R1β has also been reported to decrease binding affinity as well as coupling of the receptor to G proteins (19). A CRH-R1d isoform lacking exon 13 has been recently cloned from human myometrium (16). This isoform is poorly coupled to G proteins. Thus, it appears that CRH-R1α is the most efficient receptor isoform in transducing a CRH signal into cAMP-mediated pathways, while other isoforms either have a poor ligand-binding capacity or are poorly coupled to cAMP production. Because a spectrum of receptor isoforms expressed by a cell can determine its response to a ligand, full molecular characterization of CRH-R1 transcripts is necessary in order to understand the pleiotropic role of CRH.

Skin, the largest body organ, maintains internal homeostasis by serving as a barrier between the external environment and the internal milieu. Being continuously exposed to noxious stimuli of varying intensities, including solar radiation, thermal energy and biological agents, the skin requires a highly localized and precise mechanism for dealing with the immediacy of these interactions (20, 21). Analogous to the central response to stress centered on the HPA axis, it was proposed that similar mediators could activate peripheral responses to stress with a CRH-based signaling system playing a major regulatory role (22–24).

Both CRH and urocortin are produced in human and rodent skin, accompanied by the expression of functional CRH-R1 (21–26). It has been proposed that the flow of information involving cutaneous CRH peptides could be arranged hierarchically, from CRH through CRH-R1 to the activation of POMC peptide production and corresponding activation of the respective receptors for these peptides (22, 24). Alternatively, they could act directly through CRH-R1 activated pathways to regulate epidermal integrity, barrier function, immunomodulation, dermal vascular function, and hair growth and pigmentation (20, 22, 24). Such functional diversity requires specific molecular mediators, and functional selectivity could be achieved through differential expression of CRH-R1 isoforms.

The prior art is deficient in a full molecular characterization of CRH-R1 isoform expression for understanding the pleiotropic effects of CRH. The present invention fulfills this long-standing need and desire in the art.

SUMMARY OF THE INVENTION

In the present study, the expression of CRH-R1 isoforms was examined in various human and mouse skin samples and cell lines having different physiological and pathologic status, as well as the effects of exposure to UV radiation. The observed expression patterns were compared to pituitary, brain, adrenal and spleen CRH receptors.

Four new isoforms of human CRH-R1 (e–h) and three of mouse (mCRH-R1c, e and f) were identified. Human CRH-R1e was characterized by the deletion of exons 3 and 4; exon 12 was deleted from CRH-R1f; exon 11, 27 bp of exon 10, and 28 bp of exon 12 were deleted from CRH-R1g; and CRH-R1h was characterized by the addition of a cryptic exon. In mouse CRH-R1c, exon 3 was spliced out; in mCRH-R1e, exons 3 and 4 were spliced out; and in mCRH-R1f, exon 11 was spliced from the mRNA.

CRH-R1 was expressed in all skin specimens in patterns dependent on the cell type, physiological status and presence of pathology. CRH-R1α, the most prevalent form, was detected in almost all samples. Ultraviolet radiation (UV) changed the splicing pattern and induced or increased expression of CRH-R1g in cultured skin cells. Continuing UV treatment of succeeding generations of cells resulted in a progressive increase in the number of CRH-R1 isoforms, suggesting that receptor heterogeneity might favor cell survival. TPA, forskolin, dbcAMP and IBMX also changed the splicing patterns. These data suggest that polymorphism of CRH-R1 expression is related to anatomic location, skin physiological or pathologic status, specific cell type, and external stress (UV); and that cAMP-dependent pathways and TPA may regulate CRH-R1 expression.

In one embodiment of the current invention, a DNA encoding a corticotropin releasing hormone receptor type 1 protein amino acid is provided. This sequence may be selected from the group consisting of: SEQ ID No. 5, 6, 7, 8, 9, 10, 11, 12, 13, 14, 31, 32, 33, 34, 35, 36, and 37. Also provided is DNA encoding the protein selected from the above group, that differs from the above DNA in codon sequence due to the degeneracy of the genetic code.

In another embodiment of the current invention, the instant invention is directed to a vector capable of expressing the DNA.

The instant invention is also directed to a host cell transfected with and expressing a corticotropin releasing hormone type 1 receptor protein from such a vector.

In yet another embodiment of the instant invention, a n isolated corticotropin releasing hormone receptor type 1 protein is provided, encoded by the DNA described above. Preferably, the purified protein has an amino acid sequence corresponding to SEQ ID No: 5, 6, 7, 8, 9, 10, 11, 12, 13, 14, 31, 32, 33, 34, 35, 36, or 37.

In another embodiment of the instant invention, a n antibody directed against the corticotropin releasing hormone receptor type 1 protein is provided.

In yet another embodiment of the instant invention, a pharmaceutical composition is provided comprising a corticotropin releasing hormone receptor type 1 protein.

Still another embodiment provides a method of treating a pathophysiological state.

The present invention also provides a method of protecting skin cells against damage by inducing the expression of corticotropin releasing hormone receptor type 1g in said skin cells, wherein the expression of the corticotropin releasing hormone receptor protects said skin cells against damage induced by environmental factors, of which solar radiation is an example.

In another embodiment of the present invention, there is provided a method of screening for a compound that induces the expression of corticotropin releasing hormone receptor type 1f or 1g, comprising the steps of: contacting said compound with skin cells; and determining the expression of the corticotropin releasing hormone receptor in cells that are or are not treated with the compound, wherein increased expression of the corticotropin releasing hormone receptor in treated cells compared to untreated cells indicates the compound induces expression of the corticotropin releasing hormone receptor type 1f or 1g.

In yet another embodiment of the present invention, there is provided a method of regulating the extracellular concentration of corticotropin releasing hormone or corticotropin releasing hormone related peptides, comprising the step of: administering corticotropin releasing hormone receptor type 1e or 1h to an individual, wherein the receptor regulates extracellular concentration of corticotropin releasing hormone or corticotropin releasing hormone related peptides by binding and slowly releasing the hormone in said individual.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention as well as others which will become clear are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

FIG. 3(A–D) shows amplification of human CRH-R1 to detect transcripts (exons 2–7; primers P112 and P113).

Figure 1:
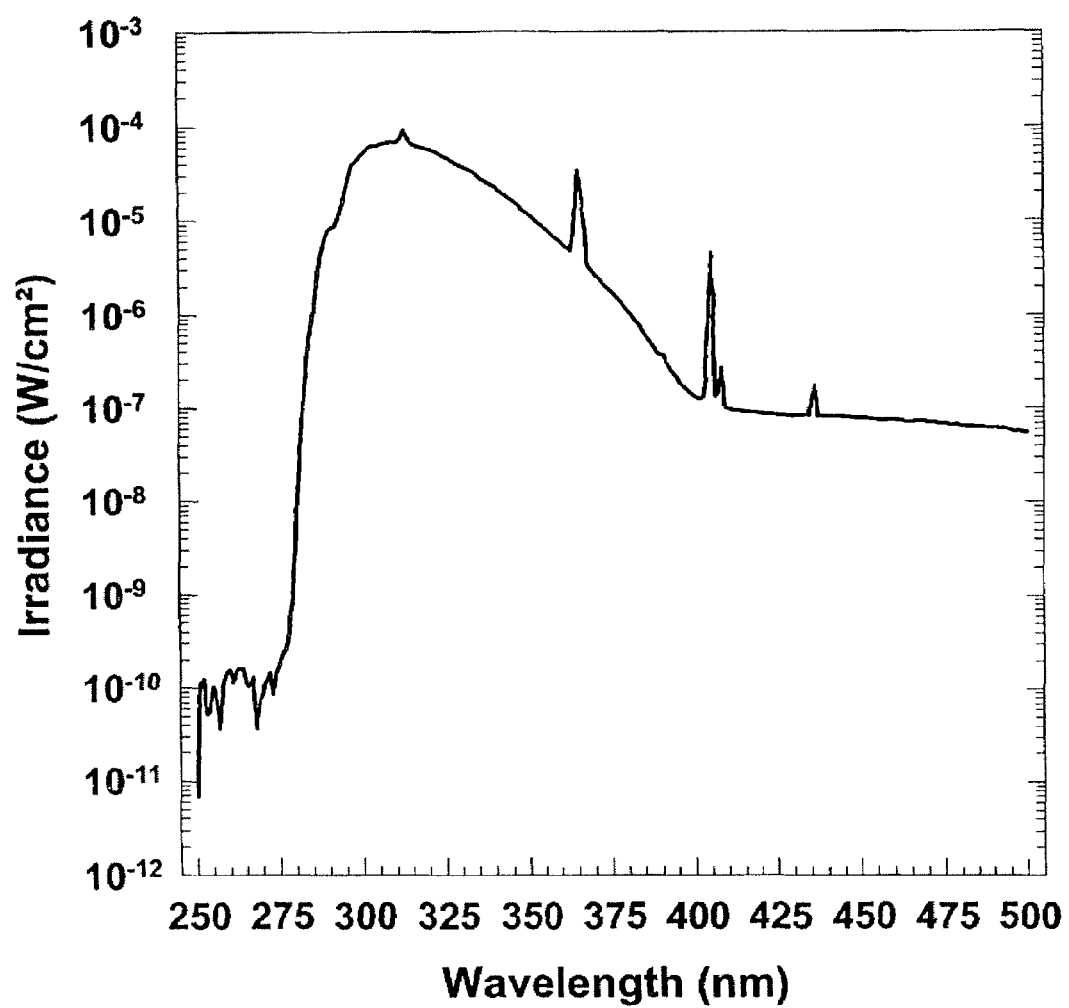
FIG. 1 shows a UV spectrum characteristic of the BioRad Transilluminator 2000 (250–500 nm).

lane 5, treated by IBMX and dbcAMP. Cells in lanes 6–8 were irradiated by 50 mJ/cm² of UVB. Lane 6, cells detached 24 hours after irradiation; lane 7, cells treated by UVB and incubated at standard conditions for 2 weeks; lane 8, two successive cycles of treatment by UVB and incubation for 2 weeks; lane 9, three successive cycles of treatment by UVB and incubation for 2 weeks; lane 1, DNA ladder. Arrows indicate sequenced bands.

Figure 4A:
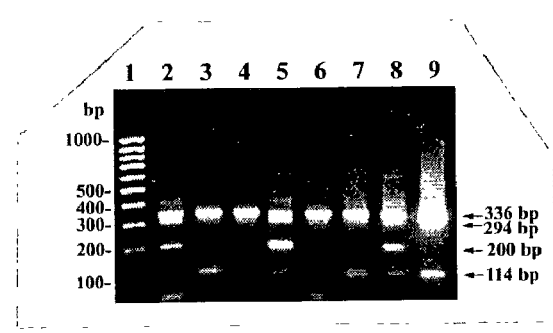
FIG. 4A shows results of screening human tissue samples: lane 2, pituitary; lane 3, adrenal gland; lane 4, normal skin; lane 5, neonatal keratinocytes; lane 6, neonatal melanocytes; lanes 7–9, skin containing basal cell carcinomas; lane 1, DNA ladder. Arrows indicate sequenced bands.
Figure 4B:
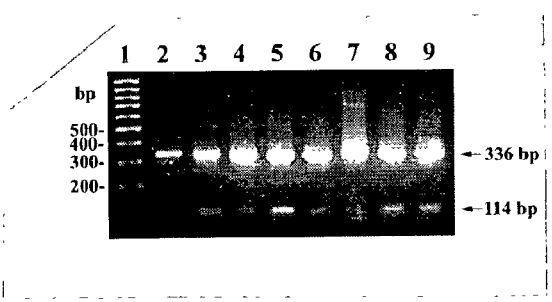
FIG. 4B shows expression in the immortalized human keratinocyte HaCaT cell line: lane 2, untreated cells (control); lane 3, treated by TPA; lane 4, treated by forskolin.
Figure 4C:
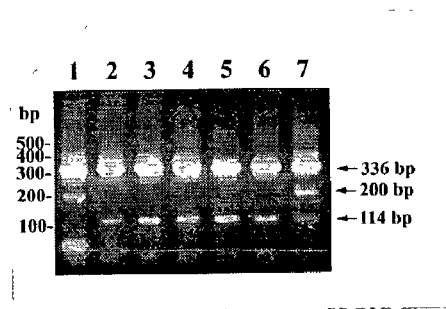
FIG. 4(A–E) shows amplification of human CRH-R1 (exons 9–14) or hamster CRH-R1 (exons 8–13) to detect transcripts.

FIG. 4C shows expression in the human squamous cell carcinoma cell line $C_{4-1}$: lane 1, untreated cells (control); lane 2, treated by TPA; lane 3, treated by forskolin; lane 4, treated by IBMX and dbcAMP. Cells in lanes 5–8 were irradiated by 50 mJ/cm² of UVB. Lane 5, cells detached 24 hours after irradiation; lane 6, cells treated by UVB and incubated at standard conditions for 2 weeks; lane 7, two successive cycles of treatment by UVB and incubation for 2 weeks. Arrows indicate sequenced bands.

Figure 4D:
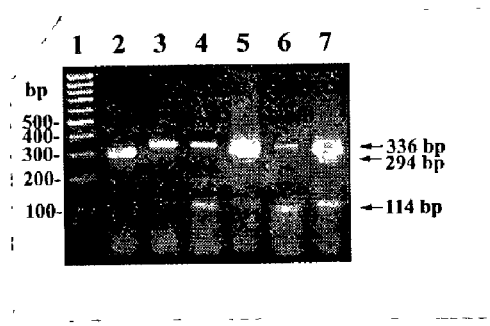

FIG. 4D shows expression in human melanoma cell line SKMEL188: lane 2, untreated cells (control); lane 3, treated by TPA; lane 4, treated by forskolin; lane 5, treated by IBMX and dbcAMP. Cells in lanes 6–7 were irradiated by 50 mJ/cm² of UVB. Lane 6, cells detached 24 hours after irradiation; lane 7, cells treated by UVB and incubated at standard conditions for 2 weeks; lane 1, DNA ladder. Arrows indicate sequenced bands.

Figure 4E:
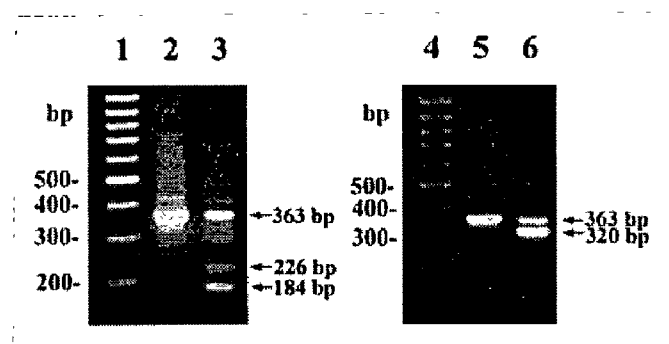

FIG. 4E shows expression in the hamster melanoma cell line AbC1. Lines 2 and 5, untreated AbC1 cells; 3, AbC1 cells irradiated by UV (50 mJ per cm² of UVB); 6, AbC1 cells after induction of melanogenesis. Lines 1 and 4, DNA ladder. Arrows indicate sequenced bands. The bands are described in Table 1.

FIG. 5(A–E) shows the predicted amino acid sequences of human CRH-R1e (GenBank Accession No. AF369651), CRH-R1f (AF369652), CRH-R1g (AF369653), and CRH-R1h (AF374231); mouse CRH-R1c (AF369654), CRH-R1e (AF369655) and CRH-R1f (AF369656); and hamster CRH-R1e (AF387669), CRH-R1f (AF387671), CRH-R1h (AF387667), CRH-R1j (AF387668), CRH-R1k (AF387670), CRH-R1m (AF387672), and CRH-R1n (AF387673) isoforms. FIG. 5A–5C shows human and mouse sequences. Previously sequenced isoforms are shown for comparison: human CRH-R1α (L23332), CRH-R1β (L23333), CRH-R1c (U16273), CRH-R1d (AF180301), and mouse CRH-R1α (NM_007762). Arrows indicate the positions of introns. The putative transmembrane domains are indicated by rows of # symbols above the appropriate amino acids. The numbers in the right-hand column refer to the amino acid number. Underlined are new sequences after the frame shift. FIG. 5D–5E shows hamster sequences. Previously sequenced isoforms are shown for comparison: hamster CRH-R1α (AY034599), and hamster CRH-R1d (AF416616). Arrows indicate the positions of introns. The putative transmembrane domains are indicated by rows of # symbols below the appropriate amino acid. The numbers in the right-hand column refer to the amino acid number. Predicted amino acid sequences situated after the frameshift are underlines. Dots represent untranslated sequences.

FIG. 6(A–D) shows amplification of mouse and hamster CRH-R1 to detect transcripts. FIG. 6A shows amplification of the mouse fragment spanning exons 2–6 (primers P158 and P159): lane 2, mouse brain; lane 3, mouse pituitary; lanes 4–6, mouse anagen IV, V and VI skin respectively; lane 7, mouse spleen. FIG. 6B shows amplification of the mouse fragment spanning exons 8–13 (primers P162 ' and P163): lane 2, mouse brain; lane 3, mouse pituitary; lanes 4–6, mouse anagen IV, V and VI skin respectively; lane 7, mouse spleen; lane 8, mouse melanoma S91 (subline M3). Lane 1 on both pictures represents DNA ladder. Arrows indicate sequenced bands. FIG. 6C shows amplification of the hamster fragment spanning exons 2–6: 2, eye; 3, pituitary; 4, heart; 5, skin; 6, melanoma Ma; 7, melanoma MI; 8, melanoma AbC1. FIG. 6D shows amplification of the hamster fragment spanning exons 8–13 (primers P162 and P163):2, eye; 3, pituitary; 4, heart; 5, spleen; 6, skin; 7, melanoma Ma; 8, melanoma MI; 9, melanoma AbC1. Lane 1 in FIGS. 6C and 6D is a DNA ladder; arrows indicate sequenced bands.

Figure 7A:
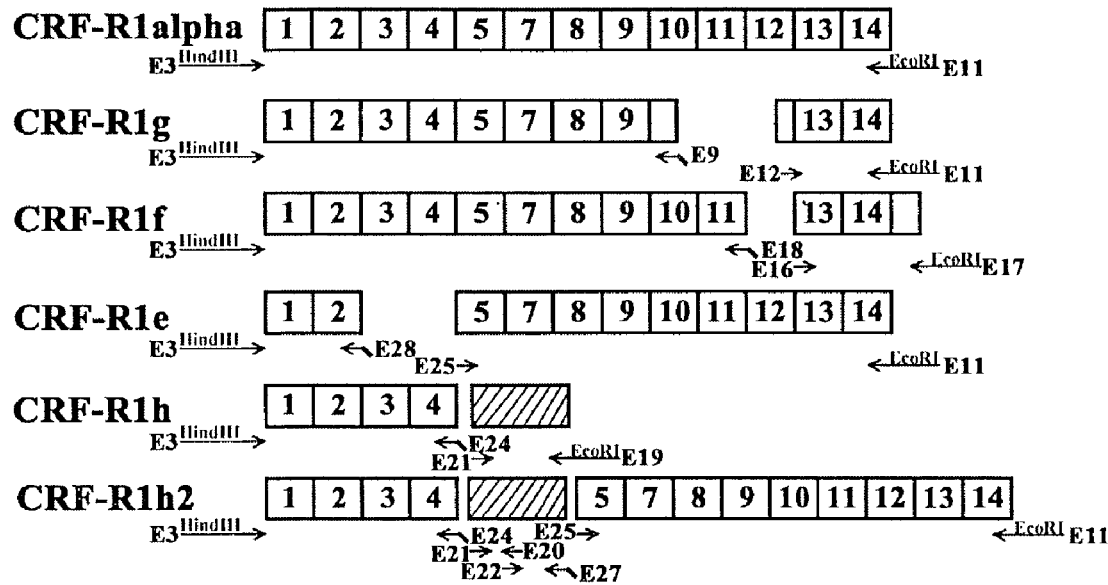
Figure 7B:
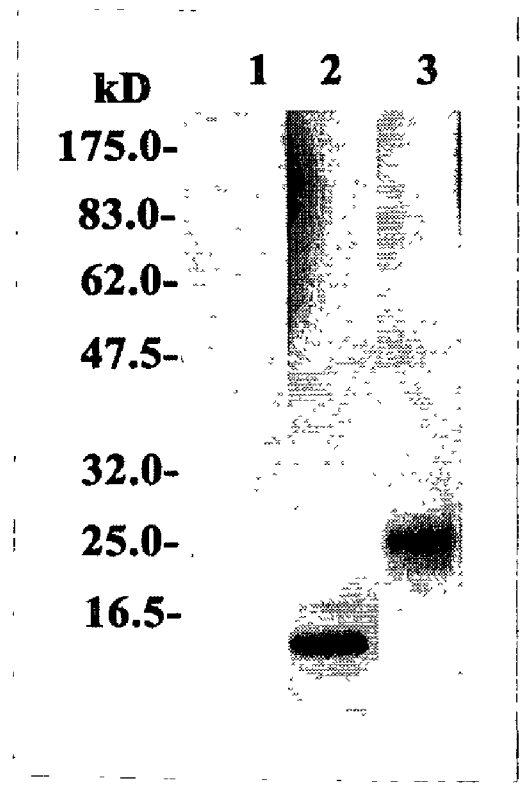
Figure 7C:
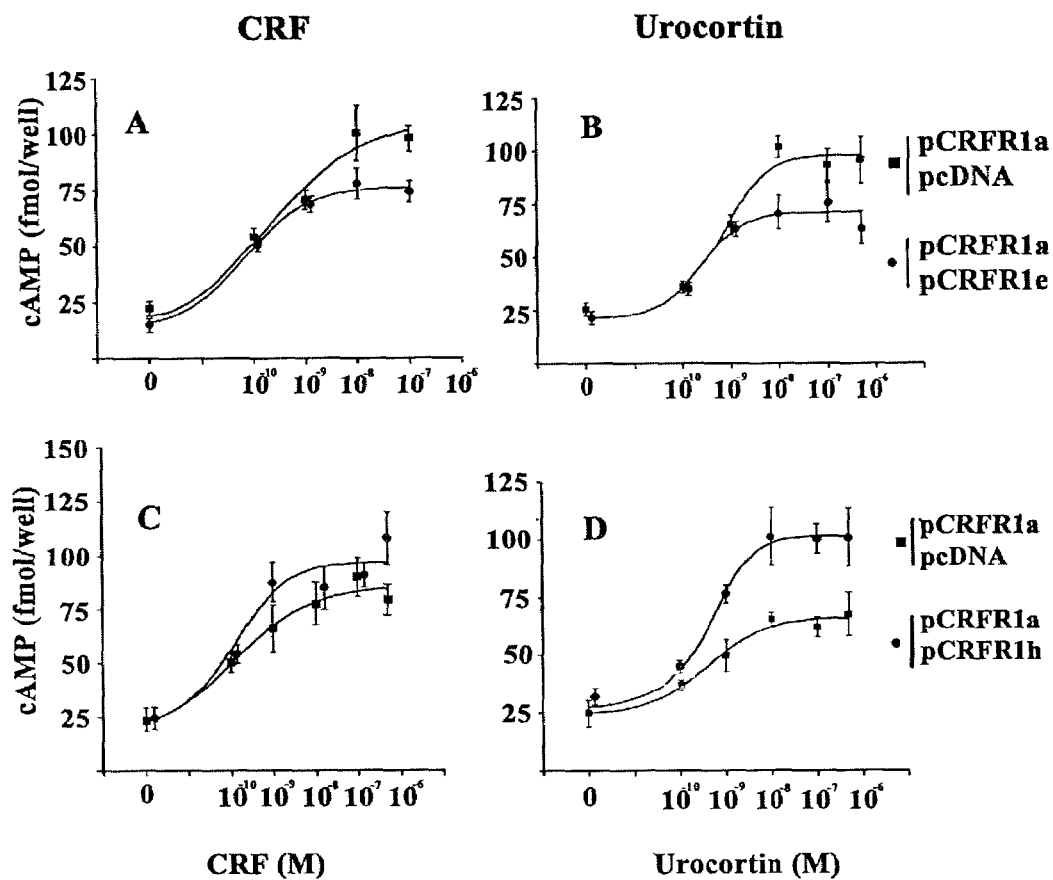

FIG. 7(A–C) shows that the CRH-R1e and CRH-R1h isoforms are translated into biologically active proteins that inhibit cAMP induction by CRH-R1α in COS stimulated with either CRH or urocortin. FIG. 7A shows expression constructs containing different isoforms of CRH-R1 (equivalent to CRF-R1). Open boxes represent exons. Arrows indicate the positions of primers used for assembling the constructs. HindIII and EcoRI restriction sites are situated in the flanking primers. Isoforms amplified by the flanking primers were cloned in the expression vector. Constructs were named according to the isoforms they contain: pCRFR1α (CRH-R1α isoform), pCRFR1g, pCRFR1f, pCRFR1e, pCRFR1h, pCRFR1h2 (CRH-R1h with 2 mutations). FIG. 7B shows Western blot analysis of expression of the CRH-R1e and CRH-R1h isoforms in transiently transfected COS cells. Samples of protein extracts of untransformed COS cells (lane 1) and cells transformed by pCRFR1e1-V5 (lane 2) or pCRFR1h-V5 (lane 3) were probed with mouse anti-V5 antibody and anti-mouse HRP. FIG. 7C shows that coexpression of CRH-R1α with CRH-R1e or CRH-R1h inhibits cAMP accumulation mediated by CRH-R1α, in CRF (I, III) or urocortin (II, IV) stimulated COS cells. COS cells were cotransfected by pCRFR1e and pCRFR1α (I and II) or by pCRFR1h and pCRFR1α (III and IV). pCRFR1c was used in all experiments as a positive control. pcDNA was used as an empty vector.

DETAILED DESCRIPTION OF THE INVENTION

Four isoforms of the human CRH receptor type 1 have been described: CRH-R1α (lacking exon 6), CRH-R1β (containing all 14 exons), CRH-R1c (lacking exons 3 and 6) and CRH-R1d (lacking exons 6 and 13). In the mouse, only one isoform equivalent to human CRH-R1α has been characterized (7).

Figure 2:
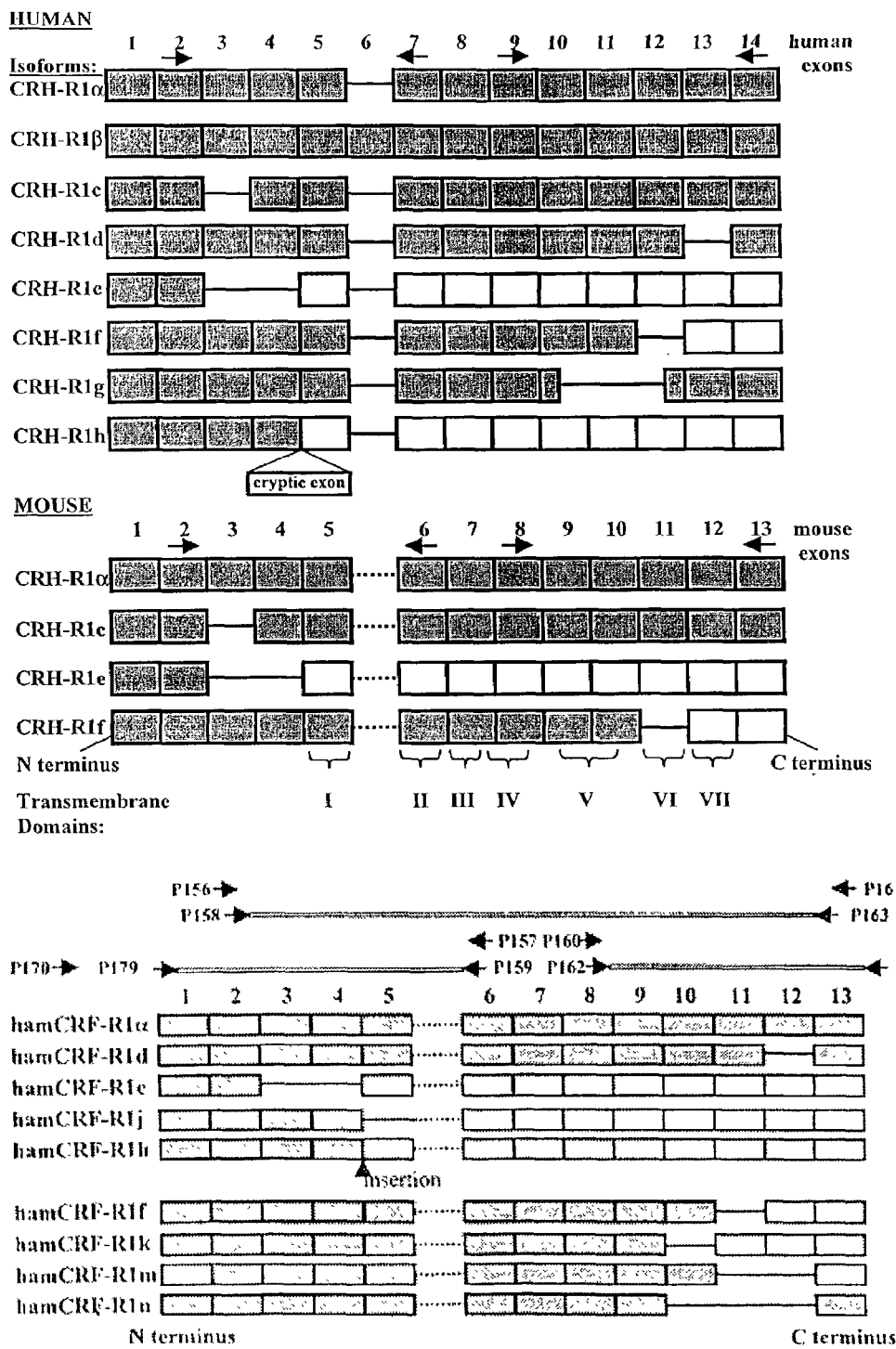
FIG. 2 shows alternatively-spliced isoforms of CRH-R1. Shadowed boxes: translated exons; open boxes: exons situated after a frame-shift; lines: exons absent in mRNA; dashed lines: homologue of human exon 6, which is not detected in mouse or hamster mRNA. The site of insertion of a cryptic exon in CRH-R1h is indicated. Arrows indicate positions of primers.

In the present study four new types of human CRH-R1 mRNA (hCRH-R1e, f, g and h) and three new mouse isoforms homologous to human CRH-R1c, e and f were identified (mCRH-R1c, e and f). In addition, seven new hamster isoforms were identified (hamCRH-R1e, f, h, j, k, m and n). Isoforms e, f, and h are homologous to the corresponding human isoforms, while j, k, m and n have so far only been identified in the hamster. In humans, in addition to exon 6, exon 12 was spliced from CRH-R1f; exons 3 and 4 were spliced from CRH-R1e; exon 11, 27 bp of exon 10 and 28 bp of exon 12 were spliced from CRH-R1g; and CRH-R1h had a cryptic exon, i.e., an insertion 110 base pairs between exons 4 and 5 (FIG. 2). The mouse and hamster sequences do not contain exon 6. Exon 3 was spliced out in mCRH-R1c; exons 3 and 4, were spliced out in mCRH-R1e, and exon 11 was missing in mCRH-R1f. The hamster hamCRH-R1e and f splicing patterns are similar to those of the mouse. (FIG. 2). Among the additional hamster isoforms, exon 5 is spliced out of hamCRH-R1j, exon 10 is spliced out of isoform k, exons 11–12 are spliced out of the m isoform, and exons 10–12 are spliced out of isoform n. The hamster h isoform, similar to the human homologue, contains a sequence inserted between exons 4 and 5.

Alternative splicing is a tightly regulated process, generating different mRNAs and increasing the coding capacity of genes (34–36). Approximately 33–59% of human genes have at least two variants (37). For example, 576 possible alternative forms of a K+ channel are expressed in a gradient along the 10,000 sensory-receptor cells present in the inner ear of birds, enabling perception of different sound frequencies (38). Furthermore, 15% of the point mutations that cause diseases in humans alter the normal splicing pattern of genes(36, 39). Thus, the described spectrum of CRH-R1 isoforms in human and mouse may reflect the diverse phenotypic functions of CRH and related peptides, requiring precise and selective coupling of signal transduction pathways.

Some information on the potential role(s) of the new isoforms in phenotypic regulation can be obtained from the analysis of predicted structures of the protein products and the gene expression patterns in different cellular compartments (FIG. 5, Table 2). Human and mouse CRH-R1e isoforms of the CRH-R1 receptor contain two reading frames. One reading frame (CRH-R1e1) encodes a soluble protein of 194 amino acids in humans and 139 amino acids in mice. It contains the first 40 amino acids of the N-terminal sequence, the remaining sequence being different from the CRH-R1 receptor due to the frame shift. Because it contains the first 400 amino acids from the N terminus, it can act either as a CRH or CRH-related peptide-binding protein. The second frame (CRH-R1e2) encodes a human protein of 240 amino acids and a mouse protein of 309 amino acids. The beginning of the protein sequence contains the third transmembrane domain in humans, and the first transmembrane domain in the mouse (FIG. 5). It will not be able to bind a ligand because it lacks the N terminus of the receptor. Similarly, the newest CRH-R2 isoform detected in the stomach also comprises only the C-terminal part of the CRH-R2 gene (GenBank accession No. E12750; (40)).

The CRH-R1h isoform encodes a truncated protein having only the CRH-binding domain (coded by exons 1–4), because the cryptic exon 4 contains a translation terminator (FIG. 5). It can potentially interfere with the binding of CRH or serve as an analog of a CRH-binding protein. Of note, tested mouse tissues did not express the CRH-R1g and CRH-R1h forms, emphasizing interspecies differences.

CRH-R1e and CRH-R1h contain sequences leading to premature termination of translation, consequently producing soluble forms of the receptor containing a CRH-binding domain. These proteins can therefore act as regulators of extracellular concentrations of CRH or CRH-related peptides by (i) making them unavailable for interaction with cell surface receptors; (ii) acting as transporters in systemic circulation or as slowly-releasing deposits of bound CRH and CRH-related peptides; or (iii) protecting them from degradation and making them available for phenotypic action in the periphery. Thus, the soluble protein products of CRH-R1e and CRH-R1h can be injected intravenously to control systemic levels of CRH and CRH-related peptides, or serve as slow-releasing deposits after intravenous or intratissue injection of complexes of receptor-ligand. Since others postulate that CRH in the periphery acts as an immunostimulator, these soluble forms can act as immunomodulators by binding to or storing the corresponding ligands. In the skin, these forms can be used to treat inflammatory skin diseases such as psoriasis, allergic contact dermatitis and others. These isoforms can also be used to regulate hair growth, because there is differential expression of these genes in the skin in relation to the growing (anagen) or resting (telogen) phases of hair follicles. The presence of the soluble protein product of the CRH-R1h gene in the pituitary suggests that it can control availability of CRH for regulation of POMC expression and production of ACTH and beta-endorphin, thus acting as a modulator of the systemic stress response.

Human CRH-R1f encodes the entire CRH-binding domain and the first five transmembrane domains; therefore, it should bind CRH and fix it on the outer surface of the cellular membrane. Thus, it may decrease the local concentration of CRH or serve as a pool of bound hormone. The murine form of this receptor also encodes the entire N-terminus and the first five transmembrane domains. The type of signal transduction pathway to which it is coupled remains to be investigated.

The most unusual isoform identified in the present study was CRH-R1g, in which the reading frame was preserved; but the protein sequence had a deletion of 74 amino acids corresponding to transmembrane domains 5 and 6. This kind of receptor can be potentially coupled to the production of cAMP.

Receptor forms CRH-R1f and CRH-R1g can serve as targets for screening the most efficient drugs that can regulate the function of neuroendocrine cells and the phenotypes of skin and immune cells through CRH receptors. Expression of the CRH-R1f and CRH-R1g isoforms also suggests that their activation by a selective ligand can inhibit keratinocyte proliferation. Their activity can play a role in hyperproliferative epidermal disorders and in regulation of hair growth, because CRH-R1f is expressed in anagen (hair follicles in growing phase) but not in telogen skin (hair follicles in resting phase).

Because expression of CRH-R1g can be induced by ultraviolet light in skin cells, it is assumed that the activity of this receptor plays a role in protection against damage induced by solar radiation. Therefore, the specific activation of this receptor by a drug can inhibit epidermal carcinogenesis or malignant transformation of epidermal or dermal melanocytes.

In one embodiment of the current invention, a DNA encoding a corticotropin releasing hormone receptor type 1 protein amino acid is provided. This sequence may be selected from the group consisting of: SEQ ID No. 5, 6, 7, 8, 9, 10, 11, 12, 13, 14, 31, 32, 33, 34, 35, 36, or 37. Also provided is DNA encoding the protein selected from the above group, that differs from the above DNA in codon sequence due to the degeneracy of the genetic code.

In another embodiment of the current invention, the instant invention is directed to a vector capable of expressing the DNA. Such a vector consists of said DNA encoding a corticotropin releasing hormone receptor type 1 protein and regulatory elements necessary for expression in a cell. The instant invention is also directed to a host cell transfected with and expressing a corticotropin releasing hormone type 1 receptor protein from such a vector. The protein may be expressed in a cell type selected from bacterial cells, mammalian cells, plant cells and insect cells. In one preferred embodiment, the protein is expressed in *E. coli*.

In yet another embodiment of the instant invention, a n isolated corticotropin releasing hormone receptor type 1 protein is provided encoded from DNA as described above. Preferably, the purified protein has an amino acid sequence corresponding to SEQ ID No: 5, 6, 7, 8, 9, 10, 11, 12, 13, 14, 31, 32, 33, 34, 35, 36, or 37.

In another embodiment of the instant invention, an antibody directed against the corticotropin releasing hormone receptor type 1 protein is provided. This antibody may be a monoclonal antibody.

In yet another embodiment of the instant invention, a pharmaceutical composition is provided comprising a corticotropin releasing hormone receptor type 1 protein. Such a pharmaceutical composition may be used to treat a pathophysiological state; in one embodiment, such a state may be a hyperproliferative epidermal disorder, allergic contact dermatitis, autoimmune disorder, epidermal carcinogenesis, or malignant transformation of epidermal or dermal melanocytes.

The present invention also provides a method of protecting skin cells against damage by inducing the expression of corticotropin releasing hormone receptor type 1g in said skin cells, wherein the expression of the corticotropin releasing hormone receptor protects said skin cells against damage induced by environmental factors, of which solar radiation is an example. The damage in this scenario will include mutagenic or carcinogenic effects, or oxidative damage to cellular components that may cause an inflammatory or autoimmune response. This may be achieved by inhibition of cell proliferation that would protect DNA by keeping it longer in the chromatin-bound form or an increase in the controlled death of damaged cells, thus, preventing oncogenesis or induction of autoimmune processes. In one embodiment, the expression of receptor type 1g in skin cells regulates production of cAMP.

In another embodiment of the present invention, there is provided a method of screening for a compound that induces the expression of corticotropin releasing hormone receptor type 1f or 1g, comprising the steps of: contacting said compound with skin cells; and determining the expression of the corticotropin releasing hormone receptor in cells that are or are not treated with the compound, wherein increased expression of the corticotropin releasing hormone receptor in treated cells compared to untreated cells indicates the compound induces expression of the corticotropin releasing hormone receptor type 1f or 1g. The expected effects in the skin would include regulation of proliferation or immune functions, or modification of the activity of other isoforms such as CRH-R1α. In one embodiment, said compound comprises a treatment for a pathophysiological state. In a preferred embodiment, the pathophysiological state is a hyperproliferative epidermal disorder or a neuroendocrine disorder.

In yet another embodiment of the present invention, there is provided a method of regulating the extracellular concentration of corticotropin releasing hormone or corticotropin releasing hormone related peptides, comprising the step of: administering corticotropin releasing hormone receptor type 1e or 1h to an individual, wherein the receptor regulates extracellular concentration of corticotropin releasing hormone or corticotropin releasing hormone related peptides by binding and slowly releasing the hormone in said individual.

In still another embodiment, administering the type 1e or 1h receptor comprises a treatment for a pathophysiological state. In a preferred embodiment, the pathophysiological state is an inflammatory skin disease, which may include psoriasis, allergic contact dermatitis, or abnormal hair growth.

Another embodiment provides that the receptor type 1e or 1h may be administered to the individual by injecting said receptor type 1e or 1h intravenously. In an additional embodiment, the administration of the receptor type 1e or 1h inhibits production of cAMP in the individual.

In an additional embodiment, said receptor type 1e or 1h comprises a complex between such receptor type and a corticotropin releasing hormone or corticotropin releasing hormone related peptides. One embodiment provides that such a complex may be administered to the individual by intravenous or intratissue injection.

The following examples are given for the purpose of illustrating various embodiments of the invention and are not meant to limit the present invention in any fashion.

EXAMPLE 1

Tissues and Cell Culture

Human tissue samples included pituitary, adrenal gland, and non-lesional normal skin and pathologic skin containing basal cell carcinoma. Skin and adrenal gland specimens were obtained from tissue removed during surgery, while pituitaries were obtained from the National Hormone and Pituitary Program, NIDDK. The tissues were stored at −80° C. until the time of analysis. The University of Tennessee Health Science Center (UTHSC) Committee on Research Involving Human Subjects approved the use of human tissues.

Murine samples consisted of brain, pituitary, spleen, and skin isolated at telogen and anagen IV, V and VI stages of the hair cycle. Female C57BL/6 mice (8 weeks old) were purchased from Taconic (NY) and housed in community cages at the animal facilities of the Albany Medical College (AMC), Albany, N.Y. The animals were sacrificed under pentobarbital anesthesia, and selected organs a s well as back skin were collected following protocols described previously (23, 27). Tissue specimens were frozen rapidly in liquid nitrogen and stored at −80° C. until further analysis. The Institutional Animal Care and Use Committee at AMC originally approved the experimental protocol, and a similar protocol for mice was approved at UTHSC.

The tissues were pulverized in liquid nitrogen with a mortar and then suspended in Trizol (Gibco-BRL, Gaithersburg, Md.), and RNA was isolated following the manufacturer's protocol.

Hamster eyes, pituitary, heart, spleen, and skin were used for the hamster studies. Syrian hamsters (males 3 months old) were purchased from Taconic (New York) and housed in community cages at the animal facilities of the Albany Medical College (AMC), Albany, N.Y. The animals were killed under pentobarbital anesthesia and selected organs as well as back skin were collected following protocols routinely used in the laboratory (47). Tissue specimens were frozen rapidly in liquid nitrogen. Hamster Bomirski Ma melanotic, MI hypomelanotic and AbC1 amelanotic melanomas were propagated in male Syrian hamsters by subcutaneous inoculation of tissue suspension as described previously (48). After killing the animals, tumor tissue was freed from connective and necrotic tissues and frozen rapidly in liquid nitrogen. Hamster tissues as well as melanoma transplants were stored at −80° C. until further analysis. The experimental protocol was originally approved by the Institutional Animal Care and Use Committee at AMC.

Human and mouse cell lines were cultured according to standard protocols as described previously, and the media were changed every second day (28, 29). The $CO_2$ concentration was 5% except for mouse normal melanocytes (see below). Human immortalized keratinocytes (HaCaT) and squamous cell carcinoma cells ($C_{4-1}$) were propagated in DMEM medium (GIBCO), while human melanoma (SK-MEL188) and mouse Cloudman S91 melanoma (sublines #6 and M3) cells were grown in Ham's F10 medium as described previously. The media were supplemented with 10% fetal bovine serum and antibiotics (GIBCO) (28, 29). Additional human melanoma cells included those established from the radial growth phase (WM 35 and SBCE2), vertical growth phase (WM 98 and WM 1341D) and metastatic phase (WM 164) (gift of Dr. M. Herlyn, Wistar Institute, Philadelphia, Pa.). These cells were cultured in DMEM supplemented with 10% fetal bovine serum, insulin (5 μg/ml) and antibiotics.

Immortalized normal mouse skin melanocyte line Me1A (from Dr. D. Bennett, Saint George Hospital, London, England) was cultured in RPMI 1640 medium supplemented with 10% bovine serum and 200 nM TPA (phorbol 12-myristate 13-acetate) in the presence of 10% $CO_2$. Normal human neonatal keratinocytes from passages 2 and 3 were used for experiments (25). Primary cell cultures were established from foreskin as described previously (25). The cells were propagated in low-calcium (0.15 mM) serum-free Keratinocyte Growth Medium (KGM) containing bovine pituitary extract (BPE) and antibiotics (Clonetics Corp., San Diego, Calif.). Normal human neonatal melanocytes were cultured in medium 154 (Cascade Biologicals, Portland, Oreg.) supplemented with 5% FBS, 13 μg/ml BPE, and 8. nM TPA, 1 μg/ml α-tocopherol, 0.6 ng/ml basic fibroblast growth factor, 1 μg/ml transferrin and 5 μg/ml insulin (all from Sigma)(30). After washing with PBS, melanoma cells were detached with Tyrode's solution containing 1 mM EDTA (28), while keratinocytes and normal melanocytes were trypsinized (26, 29).

The cells were centrifuged and suspended in RNA isolation solution (Trizol reagent).

Bomirski AbC-1 hamster melanoma cells were grown in Ham's F10 medium as described previously; the media were supplemented with 10% fetal bovine serum and antibiotics (Gibco BRL, Gaithersburg, Md.) (49). To induce melanogenesis the cells were cultured for 3 days in Dulbecco's minimal Eagle's medium plus 10% fetal bovine serum. Melanoma cells were detached with. Tyrode's solution containing 1 mM ethylenediamine tetraacetic acid after prior washing with PBS (49). The cells were centrifuged at 4° C., washed with cold PBS and cell pellets were used for RNA isolation.

In some experiments, SKMEL188, HaCaT and $C_{4-1}$ cells were also treated with TPA, forskolin or a mixture of IBMX (3-isobutyl-1-methylxanthine) and dbcAMP (N6, 2'-O-dibutyryladenosine 3':5'-cyclic monophosphate sodium) (all from Sigma). Briefly, the cells were transferred to 75 cm² flasks ($10^6$ cells/flask) and cultured for 24 hours in standard culture medium. Then the following compounds were added to the separate cultures: TPA (200 nM), forskolin ($10^{-5}$ M), IBMX ($5 \times 10^{-4}$ M), and dbcAMP ($10^{-3}$ M). Controls were represented by untreated cultures. The cells were incubated for 24 hours, detached, collected by centrifugation, and dissolved in RNA isolation solution (Trizol reagent).

COS cells were propagated in DMEM medium (GIBCO) supplemented with 10% Fetal Bovine serum and antibiotics (GIBCO). Ten thousand cells were routinely transfected in each well of opaque 96-well plate (Packard) by Lipophectamine (Invitrogen, Carlsbad, Calif.) according to the manufacturer's protocol.

EXAMPLE 2

Irradiation of Cell Lines by UV

SKMEL188, HaCaT, $C_{4-1}$ and hamster AbC1 cells were exposed to ultraviolet radiation produced by a UV transilluminator 2000 (BioRad). Cells were transferred to 9 cm Petri dishes at a concentration $10^6$ cells/dish and grown for 24 hours under standard conditions as described above. Before irradiation, the medium was aspirated and replaced by 10 ml of PBS. The dishes were placed on the UV transilluminator and incubated for 3, 12 or 31 seconds, corresponding to 5, 20 or 50 mJ/cm² doses of UVB respectively. Times of exposure and the corresponding UV, doses were calculated by the standard formula: Time (s)=Dose (J/cm²)/Intensity (W/cm²)

The spectrum of UV irradiation of the transilluminator 2000 was measured using an Optronic spectroradiometer, model 754 (FIG. 1). The calculated intensity of UVB was $1.58 \times 10^{-3}$ W/cm², that of UVA was $1.16 \times 10^{-3}$ W/cm², and that of WVC was $2.26 \times 10^{-5}$ W/cm².

After irradiation, the PBS was replaced by standard culture medium. Cells were incubated for 24 hours, detached, collected by centrifugation and dissolved in RNA isolation solution (Trizol reagent). Alternatively, cells were cultured in standard medium for 2 weeks until their full recovery. At this point cells were collected for RNA isolation or irradiated by an additional UV dose (50 mJ/cm² of UVB). The irradiated cells were then incubated for two additional weeks in standard medium until full recovery and then irradiated again. The process of UV irradiation was repeated three times.

EXAMPLE 3

RNA Extraction, cDNA Preparation and Polymerase Chain Reaction

Total RNA was extracted using a Trizol isolation kit (Gibco-BRL, Gaithersburg, Md.). The synthesis of first-strand cDNA was performed using the Superscript preamplification system (Gibco-BRL). Five μg of total RNA per reaction was reverse transcribed using oligo(dT) as the primer.

Nested PCR was used to detect different CRH-R1 isoforms. The first round of amplification of the human CRH-R1 fragment spanning exons 2–7 was conducted using 2 μl of cDNA and primers P110: 5'-TCCGTCTCGTCAAGGC-CVVC-3' (sense) (SEQ ID No. 15) and P111: 5'-GGCT-CATGGTTAGCTGGACCAC-3' (antisense) (SEQ ID No. 16). An aliquot of the PCR mixture from the first round of amplification was transferred to a new tube, and a second round of PCR was conducted. Primers for the second round of PCR were P112: 5'-TGTCCCTGGCCAGCAACATCTC-3' (sense) (SEQ ID No. 17) and P113: 5'-AGTGGATGAT-GTTTCGCAGGCAC-3' (antisense) (SEQ ID No. 18).

Amplification of exons 9 through 14 of human CRH-R1 was done in the same way. Primers for the first round of PCR were P114: 5'-CCATTGGGAAGCTGTACTACGAC-3' (sense) (SEQ ID No. 19) and P115: 5'-GCTTGATGCTGT-GAAAGCTGACAC-3' (antisense) (SEQ ID No. 20). Primers for the second round of PCR were P116: 5'-GGGTG-TACACCGACTACATCTAC-3' (sense) (SEQ ID No. 21) and P117: 5'TCTTCCGGATGGCAGAACGGAC-3' (antisense) (SEQ ID No. 22).

Primers for the first round of amplification of the mouse CRH-R1 fragment spanning exons 2–6 were P156: 5'-TC-CGGCTCGTGAAGGCCCTTC-3' (sense) (SEQ ID No. 23) and P157: 5'-GCTCAGGGTGAGCTGGACCAC-3' (antisense) (SEQ ID No. 24). Primers for the second round of PCR were P158: 5'-TGTCCCTGGCCAGCAATGTCTC-3' (sense) (SEQ ID No. 25) and P159: 5'-AGTGGATGATGT-TCCTCAGGCAC-3' (antisense) (SEQ ID No. 26).

Primers for the first round of amplification of the mouse CRH-R1 fragment spanning exons 8–13 were P160: 5'-CCATTGGGAAACTTTACTACGAC-3' (sense) (SEQ ID No. 27) and P161: 5'-CTTGATGCTGTGGAAGCTGACTC-3' (antisense) (SEQ ID No. 28). Primers for the second round of PCR were P162: 5'-AAAAGTGCTGGTTTGGCAAACGTC-3' (sense) (SEQ ID No. 29) and P163: 5'-CTTCCGGATGGCAGAGCGGAC-3' (antisense) (SEQ ID No. 30).

Primers for the first and second rounds of amplification of exons 2–6 and exons 8–13 of hamster CRH-R1 isoforms were the same as used for the mouse.

All samples were standardized for the analysis by the amplification of housekeeping gene glyceraldehyde phosphate dehydrogenase (GAPDH). Primers for the GAPDH gene were as described by Robbins and McKinney (31). GAPDH gene expression was tested in all samples to assure the integrity of isolated RNA. Integrated DNA Technology, Inc. synthesized all primers.

The reaction mixture (25 µl) contained 2.5 mM $MgCl_2$, 0.25 of each dNTP, 0.4 µM of each primer, 75 mM Tris-HCl (pH 8.8), 20 mM $(NH_4)_2SO_4$, 0.01% Tween 20 and 0.25 µl of Taq polymerase (Promega). The mixture was heated to 94° C. for 2.5 minutes and then amplified for 35 cycles: 94° C. for 30 seconds (denaturation), 65° C. for 45 seconds (annealing) and 72° C. for 1 minute (extension).

GAPDH amplification products were separated by agarose gel electrophoresis and visualized by ethidium bromide staining according to standard protocol (23).

EXAMPLE 4

Sequencing

The identified PCR products were electrophoresed in an agarose gel, then excised from the gel and purified with a GFX PCR DNA and gel band purification kit (Amersham-Pharmacia-Biotech). PCR products were sequenced from both ends. Sequencing was performed in the Molecular Resource Center at the University of Tennessee HSC (Memphis) using an Applied Biosystems 3100 Genetic Analyzer and BigDye™ Terminator Kit. The sequence data have been submitted to the GenBank database under accession numbers AF369651, AF369652, AF369653, AF374231, AF369654, AF369655, AF369656, AF387667, AF387668, AF387669, AF387670, AF387671, AF387672, and AF387673.

EXAMPLE 5

Alternate Splicing Variants of Human Corticotropin Releasing Hormone Receptor Type 1

Figure 3A:
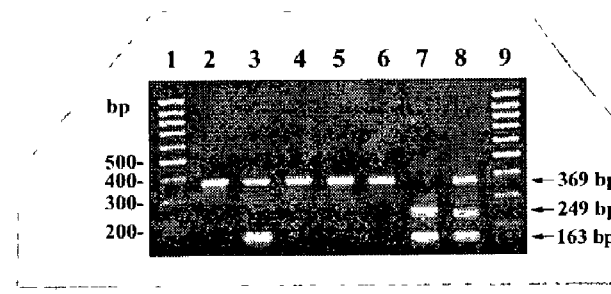
FIG. 3A shows screening of human tissue samples: lane 2, pituitary; lane 3, adrenal gland; lanes 4 and 5, normal skin samples; lane 6, normal keratinocytes; lanes 7 and 8, skin samples containing basal cell carcinomas; lanes 1 and 9, DNA ladders.

Two sets of nested primers were designed to amplify the regions of human CRH-R1 mRNA spanning exons 2 through 7 and 9 through 14 (FIG. 2). These regions contain exons 3, 6 and 13, which are more likely to be spliced out from human CRH-R1 mRNA. CRH-R1 mRNA expression was detected in all human tissues and cell lines tested including pituitary, adrenal gland, skin, normal neonatal melanocytes and keratinocytes, immortalized HaCaT keratinocytes, squamous cell carcinoma $C_{4-1}$ and melanoma cell lines (FIGS. 3A and 4A). The visualized amplification products were cut from the gels and sequenced.

The characteristics of detected isoforms are presented in Table 1. In addition to the previously described CRH-R1α, c and d isoforms, the present invention identified 4 new isoforms named CRH-R1e (AF369651), CRH-R1f (AF369652), CRH-R1g (AF369653) and CRH-R1h (AF374231). The splicing pattern is presented in FIG. 2 and Table 1. All of these isoforms have exon 6 spliced out from the final transcript. Furthermore, in CRH-R1e exons 3 and 4 are spliced out (FIG. 3A, 163 bp fragment). CRH-R1f has a deletion of exon 12 (FIGS. 4A and B, 200 bp fragment). In CRH-R1g exon 11, 27 bp of exon 10 and 28 bp of exon 12 are deleted from the mRNA transcript (FIGS. 2 and 4, 114 bp band; Table 1). CRH-R1h contains an insertion of a cryptic exon (110 bp) between exons 4 and 5 (FIG. 4B, Table 1).

Predicted protein sequences of these new isoforms in comparison to the CRH-R1 variants α, β, c and d are presented in FIG. 5. CRH-R1e and CRH-R1f have frame shifts (FIG. 2). CRH-R1e mRNA has two potential reading frames of 585 bp and 723 bp (FIG. 2, 5). The first one encodes a 194-amino acid protein (CRH-R1e1) containing only the first 40 amino acids from the N-terminus encoded by exons 1 and 2, the remaining (FIG. 5, CRH-R1e1, underlined) amino acid sequence is different from that encoded by other isoforms and does not contain transmembrane binding domains (FIG. 2, 5). The second reading frame can potentially encode a membrane-bound protein of 240 amino acids (CRH-R1e2) with a sequence starting from the third transmembrane domain and containing the C terminus (FIG. 5). The reading frame for CRH-R1f is 1113 bp long and encodes a receptor protein of 370 amino acids containing the entire CRH-binding domain and the first five transmembrane domains (215 amino acids); the remaining C terminal sequence (underlined) is different from other forms due to a frame shift (FIG. 5).

The most unusual isoform was CRH-R1g, which has preserved the reading frame of the CRH receptor. It encodes a membrane-bound protein of 341 amino acids that has a deletion of 74 amino acids corresponding to transmembrane domains 5 and 6 (FIG. 5). The insertion of a 110 bp cryptic exon between exons 4 and 5 in the CRH-R1h isoform would generate a truncated protein of 145 amino acids having only a CRH-binding domain (coded by exons 1–4), because the inserted exon contains a translation terminator (AF37423 1).

TABLE 1

Characteristics Of CRH-R1 Isoforms Detected By Nested RT-PCR

| PCR band, bp | Characteristic of PCR bands | GeneBank accession numbers |
|---|---|---|
| Human, exons 2–7 | | |
| 369 bp | Exon 6 is absent (CRH-R1α) | L23332 |
| 249 bp | Exons 3 and 6 are absent (CRH-R1c) | U16273 |
| 163 bp | Exons 3, 4 and 6 are absent (frame-shift, CRH-R1e) | AF369651 |
| 479 bp | Insertion of cryptic exon between exons 4 and 5 (CRH-R1h) | AF374231 |
| Human, exons 9–14 | | |
| 336 bp | All exons are present (CRH-R1α) | L23332 |
| 294 bp | Exon 13 is absent (CRH-R1d) | AF180301 |
| 200 bp | Exon 12 is absent (frame-shift, CRH-R1f) | AF369652 |
| 114 bp | Exon 11, 27 bp of exon 10 and 28 bp of exon 12 are absent (CRH-R1g) | AF369653 |
| Mouse, exons 2–6 | | |
| 369 bp | All exons are present (CRH-R1α) | NM_007762 |
| 249 bp | Exon 3 is absent (CRH-R1c) | AF369654 |
| 163 bp | Exons 3 and 4 are absent (frame-shift, CRH-R1e) | AF369655 |

TABLE 1-continued

Characteristics Of CRH-R1 Isoforms Detected By Nested RT-PCR

| PCR band, bp | Characteristic of PCR bands | GeneBank accession numbers |
|---|---|---|
| Mouse, exons 8–13 | | |
| 363 bp | All exons are present (CRH-R1α) | NM_007762 |
| 226 bp | Exon 11 is absent (frame-shift, CRH-R1f) | AF369656 |
| Hamster, exons 2–6 | | |
| 517 bp | Insertion of a cryptic exon between exons 4 and 5 (translation termination, CRH-R1h) | AF387667 |
| 369 bp | All exons are present (CRF-R1α) | AY034599 |
| 262 bp | Exon 5 is missing (frameshift, CRF-R1j) | AF387668 |
| 163 bp | Exons 3 and 4 are missing (frameshift, CRF-R1e) | AF387669 |
| Hamster, exons 8–13 | | |
| 363 bp | All exons are present (CRF-R1α) | AY034599 |
| 320 bp | Exon 12 is missing (CRF-R1d) | AF416616 |
| 276 bp | Exons 10 is missing (frameshift, CRF-R1k) | AF387670 |
| 226 bp | Exon 11 is missing (frameshift, CRF-R1f) | AF387671 |
| 184 bp | Exons 11 and 12 are missing (frameshift, CRF-R1m) | AF387672 |
| 98 bp | Exons 10, 11 and 12 are missing (CRF-R1n) | AF387673 |

EXAMPLE 6

Expression of Alternate Splicing Variants of Human Corticotropin Releasing Hormone Receptor Type 1

The expression pattern of CRH-R1 isoforms in tested tissues and cell lines is summarized in Table 2. CRH-R1α was the most widely expressed isoform (the 369 bp fragment in FIG. 3A; 336 bp in FIG. 4A), being detectable in pituitary, adrenal gland and in all cell lines as well as skin samples, with exception of one skin biopsy containing basal cell carcinoma. The CRH-R1c isoform was expressed only in the skin containing basal cell carcinoma (FIG. 3A, lanes 7 and 8, 249 bp fragment). The CRH-R1d isoform was detected in the pituitary, neonatal normal keratinocytes and in five melanoma lines (the 294 bp fragment in FIG. 4A, lanes 2 and 5, Table2). CRH-R1e transcripts were detected in skin containing basal cell carcinoma and in four melanoma lines, as well as hamster pituitary (Table 2). CRH-R1f transcripts were detected in one skin biopsy with basal cell carcinoma, in normal neonatal keratinocytes, a squamous cell carcinoma line and three melanoma lines, and also in hamster heart, skin, spleen, melanomas Ma and MI, and melanoma line AbC1 (Table 2). Among the newly characterized isoforms, the most widely distributed isoform was CRH-R1g that was detected in pituitary, adrenals, normal and pathologic skin, neonatal keratinocytes and five melanoma lines (Table 2). Hamster isoforms CRH-R1 j, k, and n were detected in hamster pituitary k), eye and skin (k), or eye (m). Hamster isoform m was found in melanized but not UVB-irradiated AbC1 cells (Table 2). The only isoform that could not be detected in the tested samples was CRH-R1β.

TABLE 2

Expression Of CRH-R1 In Different Tissues And Cell Lines

| Tissues and cell lines | α | β | c | d | e | f | g | h | j | k | m | n |
|---|---|---|---|---|---|---|---|---|---|---|---|---|
| Human tissues | | | | | | | | | | | | |
| Pituitary | + | | | + | | | + | + | | | | |
| Adrenal gland | + | | | | | | + | | | | | |
| Skin (5) | + | | | | | | + | | | | | |
| Skin containing basal cell carcinoma (1) | | | + | | | + | | + | | | | |
| Skin containing basal cell carcinoma (2) | + | | + | | | + | + | + | | | | |
| Human cells | | | | | | | | | | | | |
| Normal keratinocytes | + | | | + | | | + | + | | | | |
| Normal melanocytes | + | | | | | | | | | | | |
| C$_{4-1}$ (squamous cell carcinoma) | + | | | | | | + | | | | | |
| Melanoma SKMEL188 | | | | | + | | | | | | | |
| Melanoma SBCE2 | + | | | + | + | | + | + | | | | |
| Melanoma WM35 | + | | | + | + | | + | + | | | | |
| MelanomaVGP98 | + | | | | | | + | + | | | | |
| Melanoma WM164 | + | | | | + | | | + | | | | |
| Melanoma WM 1341 | + | | | + | | | + | + | | | | |
| HaCaT (immortalized keratinocytes) | + | | | | | | | | | | | |
| Mouse tissues | | | | | | | | | | | | |
| Brain | + | | | | | | + | | | | | |
| Pituitary | + | | | | | | + | | | | | |
| Anagen skin | + | | | | + | | + | + | | | | |
| Telogen skin | | | | | | | + | | | | | |
| Spleen | + | | | | + | | | | | | | |
| Mouse cells | | | | | | | | | | | | |
| Normal melanocytes | | | + | | | | | | | | | |

TABLE 2-continued

Expression Of CRH-R1 In Different Tissues And Cell Lines

| Tissues and cell lines | CRH-R1 isoforms |   |   |   |   |   |   |   |   |   |   |
|---|---|---|---|---|---|---|---|---|---|---|---|
|  | α | β | c | d | e | f | g | h | j | k | m | n |
| S91 melanoma (subline M3) | + |   |   |   |   | + |   |   |   |   |   |   |
| S91 melanoma (subline #6) | + |   |   |   |   |   |   |   |   |   |   |   |
| Hamster tissues |   |   |   |   |   |   |   |   |   |   |   |   |
| Pituitary | + |   |   |   | + |   |   |   | + |   |   |   |
| Eye | + |   |   |   |   |   |   | + |   | + |   | + |
| Heart | + |   |   |   |   | + |   |   |   |   |   |   |
| Skin | + |   |   |   |   | + |   |   |   | + |   |   |
| Spleen | + |   |   |   |   | + |   |   |   |   |   |   |
| Melanoma Ma | + |   |   |   |   | + |   |   |   |   |   |   |
| Melanoma MI | + |   |   |   |   | + |   |   |   |   |   |   |
| Hamster cells |   |   |   |   |   |   |   |   |   |   |   |   |
| Melanoma AbC1 | + |   |   |   |   | + |   |   |   |   |   |   |
| Melanoma AbC1, melanized | + |   |   |   |   | + |   |   |   | + |   |   |
| Melanoma AbC1 + UV | + |   |   |   |   |   |   |   |   |   |   |   |
| (50 mJ per cm² of UVB) | + |   |   |   |   |   |   |   |   |   |   |   |

To test the hypothesis that environmental stress can change cutaneous expression of CRH-R1 in human skin cells, as was shown in Table 2 above for hamster AbC1 cells, human HaCaT immortalized keratinocytes, SKMEL188 melanoma and $C_{4-1}$ squamous cell carcinoma cells were exposed to UV radiation. As shown in FIGS. 3–4 and Table 3, ultraviolet irradiation changed significantly the spectrum of CRH-R1 isoforms detected. In SKMEL188, UV switched expression from the CRH-R1d isoform to CRH-R1α and CRH-R1g (FIG. 4D, Table 3). In HaCaT keratinocytes, a first exposure to UV increased only expression of CRH-R1α without changing the isoform pattern (compare lanes 2 and 6 on FIG. 4B; Table 3). In $C_{4-1}$ cells, UV inhibited expression of CRH-R1f and induced the expression of CRH-R1g (FIG. 4C, lanes 1 and 5, Table 3).

Since approximately 50% of cells exposed to UV die within 3 days after treatment, cells that survived such treatment were investigated in order to establish whether a new pattern of CRH-R1 splicing is maintained in the succeeding generations. Such a pattern could represent a factor affecting the survival of cells under stressful conditions. To study these questions, CRH-R1 splicing patterns in cells that started rapid growth 2–3 weeks after UV irradiation were investigated (UV plus incubation, Table 3). Alternatively, these cultures were irradiated by a new dose of UV and again incubated for 2–3 weeks under standard conditions. It was found that the CRH-R1 splicing did not return to the original pattern (Table 3, FIG. 3B–D, FIG. 4B–D). Thus, cultured human melanoma cells preserved UV-induced CRH-R1α and CRH-R1g expression (FIG. 4D, Table 3). However, expression of the CRH-R1α isoform increased in cells cultured for 2 weeks after irradiation (compare lanes 2 and 6 in FIG. 3D and lanes 2 and 7 in FIG. 4D).

Figure 3B:
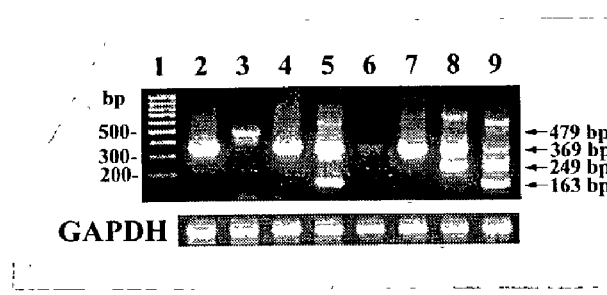
FIG. 3B shows expression in the immortalized human keratinocyte cell line HaCat: lane 2, untreated cells (control); lane 3, treated by TPA; lane 4, treated by forskolin; lane 5, treated by IBMX and dbcAMP. Cells in lanes 6–9 were irradiated by 50 mJ/cm$^2$ of UVB. Lane 6, cells detached 24 hours after irradiation; lane 7, cells treated by UVB and incubated at standard conditions for 2 weeks; lane 8, two successive cycles of treatment by UVB and incubation for 2 weeks; lane 9, three successive cycles of treatment by UVB and incubation for 2 weeks; lane 1, DNA ladder. Amplification of GAPDH is shown below the pictures. Arrows indicate sequenced bands.
Figure 3C:
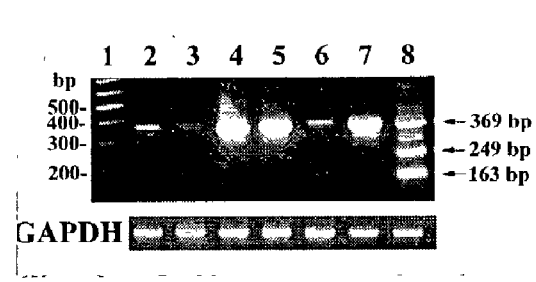
FIG. 3C shows expression in human squamous cell carcinoma $C_{4-1}$: lane 2, untreated cells (control); lane 3, treated by TPA; lane 4, treated by forskolin; lane 5, treated by IBMX and dbcAMP. Cells in lanes 6–8 were irradiated by 50 mJ/cm$^2$ of UVB. Lane 6, cells detached 24 hours after irradiation; lane 7, cells treated by UVB and incubated at standard conditions for 2 weeks; lane 8, two successive cycles of treatment by UVB and incubation for 2 weeks; lane 1, DNA ladder. Amplification of GAPDH is shown below the pictures. Arrows indicate sequenced bands.
Figure 3D:
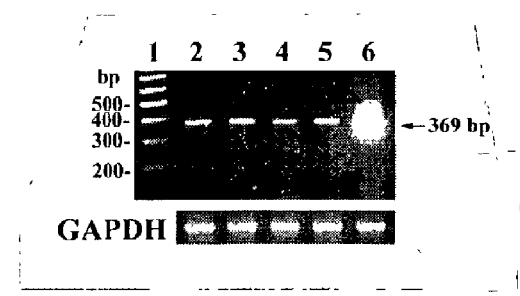
FIG. 3D shows expression in human melanoma cell line SKMEL188: lane 2, untreated cells (control); lane 3, treated by TPA; lane 4, treated by forskolin; lane 5, treated by IBMX and dbcAMP; lane 6, cells treated by UVB (50 mJ/cm$^2$) and incubated at standard conditions for 2 weeks; lane 1, DNA ladder. Amplification of GAPDH is shown below the pictures. Arrows indicate sequenced bands.

HaCaT keratinocytes gained expression of the CRH-R1c and CRH-R1g isoforms after a second UV treatment, and CRH-R1e after a third UV treatment (FIGS. 3B and 4B, Table 2). $C_{4-1}$ cells cultured for two weeks after second UV treatments expressed the CRH-R1c, CRH-R1e and CRH-R1g isoforms in addition to CRH-R1α (FIG. 3C, lane 8; FIG. 4C, lane 7). Thus, repeated exposure of the epithelial cells (HaCaT and $C_{1-4}$ cells) to UV increased the number of CRH-R1 isoforms expressed (Table 3).

To test whether cAMP-dependent and TPA-induced pathways can change CRH receptor expression, cell lines were incubated in the presence of TPA, forskolin or a mixture of IBMX and dbcAMP. Differential and cell-specific splicing patterns were observed. In human melanoma cells, TPA shifted the CRH-R1 splicing pattern from the CRH-R1d to the CRH-R1α isoform (FIG. 4D, Table 3). Forskolin or dbcAMP plus IBMX inhibited expression of CRH-R1d and stimulated expression of CRH-R1α and CRH-R1g; the pattern was identical to that induced by UV (Table 3, FIG. 4D). In the $C_{4-1}$ cell line, all of these compounds switched off CRH-R1f isoform expression and induced CRH-R1g; the pattern was again identical to that induced by UV (Table 3, FIG. 4C).

In HaCaT keratinocytes, TPA induced insertion of a 110 bp fragment between exons 4 and 5 of CRH-R1 (FIG. 3B, lane 3, 479 bp fragment) that led to a premature translation termination due to the presence of a termination codon in the inserted sequence. This isoform was named CRH-R1h (Table 1). In these cells forskolin had no effect on splicing, while dbcAMP plus IBMX induced expression of CRH-R1e and CRH-R1g (Table 3). In summary, forskolin and dbcAMP plus IBMX, but not TPA, stimulated CRH-R1g isoform expression in all cell lines tested (with the exception of HaCaT cells in the case of forskolin) (Table 3), and also increased the level of CRH-R1α expression (compare lanes 2–5 in FIG. 3C, FIG. 4B and FIG. 4D).

TABLE 3

Environmental Regulation Of CRH-R1 Expression In Human Skin Cells

| Tissues and cell lines | CRH-R1 isoforms |   |   |   |   |   |   |
|---|---|---|---|---|---|---|---|
|  | α | c | d | e | f | g | h |
| Melanoma SKMEL188 |   |   |   |   |   |   |   |
| Control |   |   | + |   |   |   |   |
| + UV | + |   |   |   |   | + |   |
| + UV + incubation | + |   |   |   |   | + |   |
| + TPA | + |   |   |   |   |   |   |
| + forskolin | + |   |   |   |   | + |   |
| + dbcAMP + IBMX | + |   |   |   |   | + |   |
| HaCaT (immortalized |   |   |   |   |   |   |   |

TABLE 3-continued

Environmental Regulation Of CRH-R1 Expression In Human Skin Cells

| Tissues and cell lines | CRH-R1 isoforms | | | | | | |
|---|---|---|---|---|---|---|---|
| | α | c | d | e | f | g | h |
| keratinocytes) | | | | | | | |
| Control | + | | | | | | |
| + UV | + | | | | | | |
| + UV + incubation | + | | | | | | |
| + 2x (UV + incubation) | + | + | | | | + | |
| + 3x (UV + incubation) | + | + | | | + | + | |
| + TPA | | | | | | | + |
| + forskolin | + | | | | | | |
| + dbcAMP + IBMX | + | | | + | | + | |
| C$_{4-1}$ (squamous cell carcinoma) | | | | | | | |
| Control | + | | | + | | | |
| + UV | + | | | | | + | |
| + UV +incubation | + | | | | | + | |
| + 2x (UVB + incubation) | + | + | | + | + | + | |
| + TPA | + | | | | | + | |
| + forskolin | + | | | | | + | |
| + dbcAMP + IBMX | + | | | | | + | |

EXAMPLE 7

Alternate Splicing Variants of Mouse and Hamster Corticotropin Releasing Hormone Receptor Type 1

Only one CRH-R1 isoform has been previously described in mice, i.e., an analog of human CRH-R1α (7). To test CRH-R1 expression patterns in the mouse, different mouse tissue samples were screened (Table 2) with a set of specific primers, in which exonal locations are listed in FIG. 2. The exonal allocation is based on the rodent (rat) gene structure that is similar to that in humans, except that it does not contain exon 6 (14, 32). The detected isoforms have been marked with the letter "m" to emphasize their murine origin, as counterparts of the human receptor form.

Amplification of mouse cDNAs showed that mRNA of mCRH-R1α was expressed in mouse brain, pituitary, spleen, mouse anagen IV, V and VI skin, normal melanocytes and Cloudman S91 melanoma cells (FIG. 6(A–B) and Table 2). The α isoform was absent in resting (telogen) skin. In addition to mCRH-R1α, three new isoforms were detected (FIG. 2, Table 1). One of them is analogous to the human CRH-R1c isoform (AF369654), lacking part of the CRH-binding domain due to the absence of exon 3 (Table 1). This isoform encodes a protein of 375 amino acids, and analogous to the human counterpart (17, 18, 33) would have a decreased affinity to CRH. It is expressed only in anagen (IV–VI) skin and spleen (FIG. 6(A–B) and Table 2). The other two isoforms are homologues of human CRH-R1e and CRH-R1f. These isoforms also have deletions of exons 3 and 4 (AF369655) or 11 (AF369656), respectively; these deletions lead to frame shifts and consequent changes in amino acid sequences of the receptor proteins (FIG. 5A–5C). Mouse CRH-R1e mRNA also has two potential reading frames of 420 bp and 930 bp (FIG. 5A–5C). The first one (mCRH-R1e1) encodes a protein of 139 amino acids that is similar to the human counterpart; it contains only first 40 amino acids from the N-terminus of CRH-R1 and lacks transmembrane domains due to a frame shift (FIG. 5A–5C, underlined). The second reading frame (mCRH-R1e2) can potentially encode a membrane-bound protein of 309 amino acids with a sequence starting from the first transmembrane domain and containing the C terminus (FIG. 5A–5C). The reading frame for CRH-R1f of 990 bp encodes a receptor protein of 329 amino acids containing the entire CRH-binding domain, seven transmembrane domains and a proximal part of the C terminus; the distal part of the C terminus is missing due to the absence of exon 12 (FIGS. 2 and 6(A–B)). mCRH-R1e is expressed in the brain, pituitary, and telogen and anagen skin, while mCRH-R1f is expressed in anagen skin and in the M3 subline of Cloudman S91 melanoma cells (Table 2).

To test CRH-R1 expression patterns in the hamster, the regions of the hamster CRH-R1 mRNA spanning exons 2–6 and 8–13 were amplified from various tissues, two melanoma types propagated in hamsters, and the AbC1 melanoma cell line (Table 2). CRF-R1 expression was detected in all hamster tissues tested, including pituitary, eye, skin, spleen, and melanoma lines (FIG. 6 (C–D)). The visualized amplification products were cut from an agarose gel and sequenced. The splicing patterns are presented in FIG. 2 and Table 1. Apart from CRF-R1α, CRF-R1e and f isoforms were also detected, and the h isoform similar to that found in humans. mRNA corresponding to the hamster, mouse, and human CRH-R1e isoform does not have exons 3 and 4 (FIG. 2). The reading frame for the hamster e isoform is 420 base pairs long and contains only the first two in-frame exons of the original receptor. It can be translated into a 129-amino acid peptide (FIG. 5D–5E). There is another potential reading frame containing seven transmembrane domains, but the biologic role of this protein is not clear. CRH-R1e was expressed only in the hamster pituitary gland (Table 2).

The hamster CRH-R1f isoform is also similar to the murine form in that it does not have exon 11 and also contains a 963-base pair long reading frame potentially translating into a 320-amino acid protein. This protein has the CRH-binding domain and also contains the first five transmembrane domains; thus, it can potentially bind CRH. Hamster CRH-R1f was expressed in skin, melanomas, heart, and spleen but not in the pituitary (Table 2).

The hamster CRH-R1h isoform was also similar to the isoform that was found in humans. Hamster CRH-R1h mRNA has a 148-base pair insertion, representing a cryptic exon between exons 4 and 5 that should lead to the production of a truncated protein (114 amino acids) due to the presence of several terminator codons (FIGS. 2 and 5D–5E). The human isoform has a 110-base pair insertion. For comparison, insertions of a cryptic exon have been found in other G protein-coupled receptors, such as the serotonin 2 A receptor (50). Both hamster and human CRF-R1h isoforms contain CRF-binding domains only. Thus this isoform may represent a soluble protein with the binding activity for CRH-related peptides.

Of great interest is the finding of new types of CRF-R1 mRNA in the hamster. CRH-R1j has a deletion of exon 5 (FIG. 6C; 276 base pair fragment), and its reading frame is 519 base pairs long, coding for a 172-amino acid peptide comprising only the CRH-binding domain (FIG. 5D–5E). Thus this isoform can encode a soluble CRH-R1 isoform with properties similar to CRH-R1h.

Exon 10 is deleted from CRH-R1k mRNA (FIG. 2; 280 base pair fragment); the reading frame is 1020 base pairs long, and it can encode a 339-amino acid peptide containing a CRH-binding domain and two transmembrane domains, lacking the C terminus of the receptor (FIG. 5D–5E). If this isoform was expressed it should be able to bind CRH and fix it on the membrane surface. mRNA corresponding to this isoform in hamster eye and skin was found (Table 2).

The CRH-R1n isoform mRNA preserves the original reading frame of the CRH receptor, although it lacks exons 10–12. This deletion does not cause a reading frameshift. The resulting protein has 327 amino acids, with complete absence of transmembrane domains 6 and 7. Nine amino acids of the fifth domain are also deleted, but the C terminus is probably inside of the cell as there are 15 amino acids of the fifth hydrophobic domain left. This composition is reminiscent of the CRF-R1g isoform found in humans. Human mRNA corresponding to CRH-F1g contains a deletion of exon 11, 27 base pairs of exon 10, and 28 base pairs of exon 12; it does not have transmembrane domains 5 and 6 but is should preserve the intracellular localization of the C terminus, as the last hydrophobic domain is present. Hamster CRF-R1n and human CRF-R1g isoforms might have properties different from other isoforms. First although their mRNAs have extensive deletions, they preserve an original reading frame and C terminus. Second, the C terminus should be situated inside the cell, allowing receptor coupling to a signal transduction pathway. On the other side, they also differ from CRF-R1c and d isoforms by having extensive in-frame deletions of either fifth and sixth or sixth and seventh transmembrane domains.

Figure 6A:
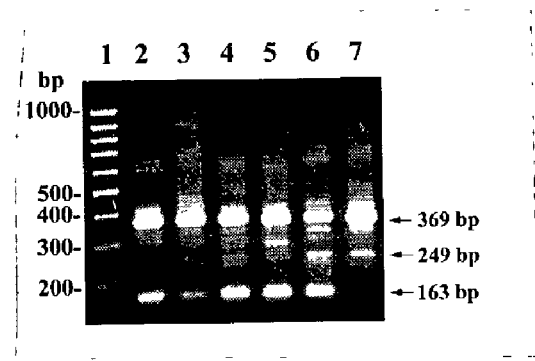
Figure 6B:
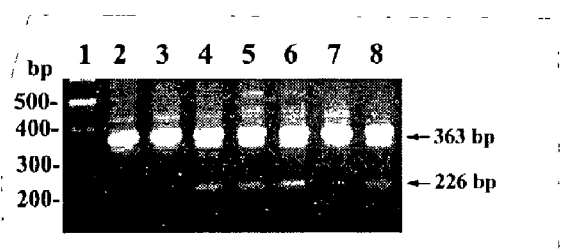
Figure 6C:
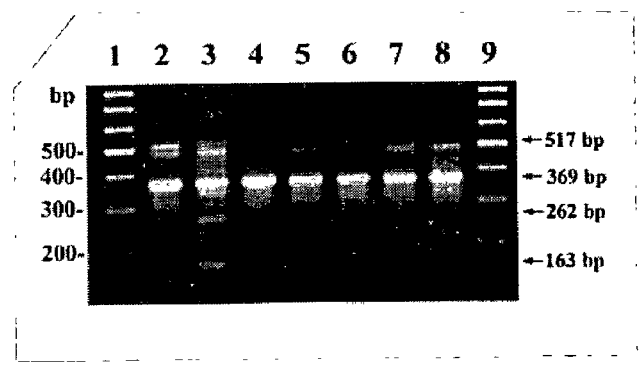
Figure 6D:
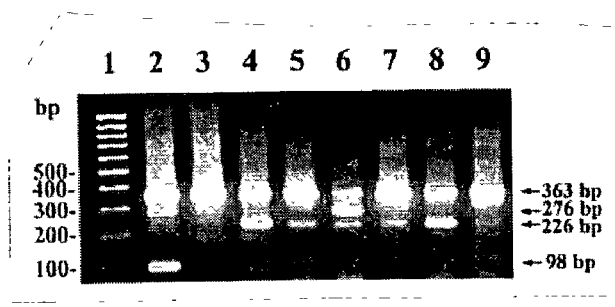

The expression patterns of CRH-R1 isoforms in tested tissues and cell lines is summarized in Table 2. CRF-R1α was expressed in all samples tested (369 base pair fragment in FIG. 6C and 363 base pairs in FIG. 6D). CRH-R1f was also widely expressed, being detected in hamster heart, skin, spleen, and melanomas (FIG. 6D, 226 base pairs; Table 2). CRH-R1e was detected only in the pituitary (FIG. 6C, lane 3, 163 base pair fragment) and CRH-R1n only in the hamster eye (FIG. 6D, lane 2, 98 base pair fragment). Isoform k was expressed in hamster eye and skin, and the j isoform only in the eye (Table 2).

Ultraviolet light is known to induce melanin synthesis in skin. Melanin synthesis is a multistep process of transformation of L-tyrosine to a melanin biopolymer that includes free radical formation and can potentially generate intracellular oxidative stress (51). The hamster AbC1 cell line was tested, which is amelanotic when cultured in Ham's F10 medium and produces melanin pigment when propagated in Dulbecco's minimal Eagle's medium (49). It was found that induction of melanin synthesis (FIG. 4E) changed the CRH-R1 splicing pattern. Thus, a 184 base pair band appeared that corresponded to an isoform, which was named CRH-R1m (Table 1). mRNA corresponding to this isoform has a deletion of exons 11 and 12, resulting in a reading frame 1071 base pairs long, and encoding a protein of 356 amino acids. As the receptor reading frame is shifted after exon 10, CRH-R1m resembles the k and f isoforms, with a CRH-binding domain and the first two transmembrane domains. UV light also changed the pattern of CRH-R1 alternative splicing but differently from the effect of melanogenesis. UV light induced expression of an additional isoform that was analogous to human CRH-R1d (FIG. 4E). This form did not have the exon 12 comprising the largest part of the seventh transmembrane domain (FIG. 2), and it was poorly coupled to cAMP production (16). As in other models, the quantity and ratios between splicing factors have a pronounced impact on splice site selection (34); by analogy, UV irradiation and melanin synthesis may act by changing splicing factor availability or activity. Although the mechanism involved in this process is unknown, the different spliced patterns evidence that different regulatory pathways activated either by UV or melanogenesis become operational.

EXAMPLE 8

Regulation and Functions of Alternate Splicing Variants of Corticotropin Releasing Hormone Receptor Type 1

Among the already described isoforms, CRH-R1α is the most efficient receptor variant in transducing a peptide signal into cAMP-mediated pathways. Other forms (β, c, and d) either have a decreased ligand binding capacity (β, c) or are poorly coupled to cAMP production (β, d) (16, 18, 19). CRH-R1α was the most prevalent form detected in almost all samples tested, with the exception of one human melanoma cell line (SKMEL188), one skin biopsy containing basal cell carcinoma, and the mouse telogen skin.

The dominant role of CRH-R1α in the skin is further emphasized by the induction of expression in human melanoma cells and keratinocytes by UV and other factors raising cAMP. There was also hair cycle-dependent expression in murine skin (present in anagen and absent in telogen). Of note, pigmentary, metabolic, endocrine and immune activities of mouse skin fluctuate during the hair cycle, being low in telogen (resting phase) and high in anagen (growing phase) (20, 21, 41). The second most frequent form detected in human tissues was CRH-R1g, which can be potentially coupled to cAMP production. Therefore, data in the present study suggest that the main pathway activated by CRH (or related peptides) in the skin involves increased production of cAMP.

CRH-R1β was not detected in samples derived from human corporal skin, suggesting lack of expression in the tested material. This is in agreement with a previous study showing the absence of CRH-R1β in corporal skin, cultured melanocytes and keratinocytes, and its restricted expression in the scalp (24). Alternatively, the negative results may be due to the preferential amplification of shorter PCR fragments. However, most of the PCR reactions produced several bands of different lengths, implying that one isoform did not completely dominate the amplification reaction. The CRH-R1α isoform, which is only 87 bp shorter, was detected in almost all tested samples. Thus, even if the CRH-R1β isoform is present in the corporal skin, the level of its expression is below the limit of detection of the PCR method.

Accepting that CRH signaling plays a central role in response to stress (20–22), it would be expected that in response to environmental stressors, the expression pattern of CRH-R1 would be changed to counteract the damaging effects of external or internal insults. The experiments with the ultraviolet irradiation that changed the pattern of receptor splicing in skin-derived cell lines support this concept. Thus, CRH-R1 mRNA splicing was changed from the d to the α and g isoforms in the human melanoma cell line; CRH-R1α and g also increased in UV-treated immortalized and malignant keratinocytes. Again, this pattern suggests that cutaneous stress stimulates the expression of isoforms that are or can be coupled to cAMP production. It is also significant that the newly gained pattern of CRH-R1 splicing appears to be stable, e.g., it does not regress even after prolonged cultivation (more that 2 weeks in culture). Although it is unclear how this splicing pattern is preserved, it suggests that this new pattern somehow promotes the survival of cells damaged by radiation. Repeated treatments by UV led to an increase of CRH-R1 isoforms expressed in normal and malignant keratinocyte lines, with the resulting populations expressing the CRH-R1c, e, and f and g isoforms in addition the initial CRH-R1α.

Thus, its appears that repeated stress favors the survival of cells having a diverse spectrum of CRH receptor isoforms, probably reflecting the induced cellular heterogeneity of these lines. By analogy with tumor biology (42), such heterogeneity could play a role in stabilizing the phenotype of the cell line, making it resistant to external manipulation. Pawelek et al. (43, 44) proposed that the melanocyte response to solar radiation is highly regulated, involving UV-stimulated expression, activation of MSH receptors and increased production of their ligands, e.g., POMC-derived MSH and ACTH. It was noted that UV induced CRH-R1 expression with preference for the most efficient α isoform, and production of the respective CRH ligand (45). Thus, this general molecular mechanism of UV action on epidermal cells (43, 44) may be conserved and would involve stimulation of CRH and POMC peptide production accompanied by induction and modification of the corresponding receptors (20, 45, 46).

To better understand the mechanism of differential CRH-R1 splicing, the effects of factors raising intracellular cAMP and of TPA were examined. Factors raising intracellular cAMP increased CRH-R1 expression and switched the pattern to predominant expression of the α and g isoforms. This pattern was similar or identical to that induced by ultraviolet radiation, suggesting that similar mechanisms regulate CRH-R1 expression that are tightly linked to a cAMP-activated signaling pathway(s). TPA also switched receptor splicing; however, the pattern of expression levels were different from those induced by UV or cAMP-dependent signals. Thus, it is suggested that cutaneous CRH-R1 gene expression can be regulated by at least two different signaling systems: one activated by UV and cAMP, and the second by TPA.

In summary, the present study finds that CRH-R1 is differentially spliced in a variety of human and mouse tissues. New isoforms of the receptors are identified, and a pattern of environmental regulation in cultured skin cells is found. In conclusion, a polymorphism of CRH-R1 expression appears to be related to anatomic location, skin physiological and pathologic status and cell type. In addition, external stress (UV), cAMP dependent pathways and TPA can also regulate CRH-R1 expression in skin cells.

EXAMPLE 9 cAMP Accumulation in CRF or Urocortin-Stimulated COS Cells

Expression constructs were prepared that contain different isoforms of CRH-R1 (FIG. 7A). The alpha isoform was amplified from the phCRF-R82 plasmid by primers E3 and E11.

Full-length CRF-R1g DNA was obtained from three PCR reactions. First, a fragment spanning the 5' untranslated sequence and exons 1 through 10 was amplified using primers E3 and E9. A second fragment (exons 12–14) was amplified using primers E12 and E11. Finally, the first and second fragments were assembled together using primers E3 and E11; this was possible because primer E9 contained a sequence homologous to primer E12.

Similarly, for the CRF-R1f construct exons 1 through 11 of the CRF receptor were amplified using primers E3 and E18, and exons 13 and 14 by using primers E16 and E17. The full sequence was obtained by combining these two fragments together using primers E3 and E17.

CRF-R1e DNA was constructed in a slightly more complicated way. Fragments spanning exons 1–2 and 5–14 were amplified using primer pairs E3, E24 and E25, E11 respectively. The first fragment was slightly extended in nested PCR by primers E3 and E28. Finally, full-length CRF-R1e DNA was assembled by amplifying these two fragments with primers E3 and E11.

The CRF-R1h isoform contained exons 1–4 and a fragment of the cryptic exon up to the translation terminator. This construct was also assembled in 3 steps. In the first step, exons 1 through 4 were amplified with primers E3 and E24; in the second step, the cryptic exon was amplified with primers E12 and E19. In the third PCR step, the final CRF-R1h DNA was assemble using primers E3 and E11.

Sequences of primers:

E3:
5'-AAAAGCTTAGGACCCGGGCATTCAGGA-3' (SEQ ID No.38)

E9:
5'-GAAGGAGTTGAAGTAGATGTAGTCGGTGTACA-3' (SEQ ID No.39)

E11:
5'-AAGAATTCTCAGACTGCTGTGGACTGCT-3' (SEQ ID No.40)

E12:
5'-CATCTACTTCAACTCCTTCCTG-3' (SEQ ID No.41)

E16:
5'-CATTCAGTACAGGGCTTCTTTGTGTCTGTG-3' (SEQ ID No.42)

E17:
5'-AAGAATTCTCATCCCCCCAGCCACAG-3' (SEQ ID No.43)

E18:
5'-ACAAAGAAGC-CCTGTACTGAATGGTCTCAG-3' (SEQ ID No.44)

E19:
5'-AAGAATTCTTTGTCCCACCACGGTGTGCTC-3' (SEQ ID No.45)

E24:
5'-CTCCTCATTGAGGATCTCCT-3' (SEQ ID No.46)

E25:
5'-CTTGCTTTTTTTGAGATGTTGCTGGCCAGGGA-3' (SEQ ID No.47)

E27:
5'-GGTAGTGCACCTTGCTTTTTTTCTCTCCCCA-3' (SEQ ID No.48)

E28:
5'-TGGTAGTGCACCTTGCTTTTTTTGAGATGTTGC-3' (SEQ ID No.49)

Receptor isoforms e and h were tested for their ability to produce soluble forms of the CRH receptor that would affect the activity of the most prevalent CRH-R1α isoform. To allow detection by immunoblotting, a cDNA for the V5 protein was attached to the cDNA for the isoforms in the constructs. The constructs were thus transfected into COS cells and tested as to whether the isoform messages were translatable, and whether cotransfection of CRH-R1α with CRH-R1e or h affects the activity of CRH-R1α.

COS cells were propagated in DMEM medium (GIBCO) supplemented with 10% Fetal Bovine serum and antibiotics (GIBCO). Ten thousand cells were routinely transfected in each well of opaque 96-well plate (Packard) by Lipophectamine (Invitrogen, Carlsbad, Calif.) according to the manufacturer's protocol.

Western blot analysis (FIG. 7B) using antibody against V5 protein shows that CRH-R1e and h are translated into final protein products (see the main bands in lines 2 and 3 of FIG. 7B). Samples of protein extracts of untransformed COS cells and cells transfected with pCRFR1e1-V5 or pCRFR1h-V5 were probed with mouse anti-V5 antibody (Invitrogen) and anti-mouse HRP.

Cyclic AMP concentration was measured by a cAMP functional assay kit (Packard BioScience, Meriden, Conn.). Stimulated cells were washed 3 times by PBS and incubated for 1 hour in 25 µl of lysis buffer at room temperature. The signal was measured using a Fusion α instrument (Packard BioScience), and cAMP concentrations were recalculated from the standard curve.

FIG. 7C shows that coexpression of CRF-R1α with CRF-R1e inhibits CRH or urocortin-stimulated cAMP accumulation mediated by CRF-R1α, and that coexpression of CRF-R1α with CRF-R1h stimulates CRH or urocortin-stimulated cAMP accumulation mediated by CRF-R1α.

Taken together, FIGS. 7B and 7C demonstrate that CRH-R1e and CRH-R1h are translated into final biologically active proteins. The soluble CRF-R1e would bind the receptor ligand, thereby decreasing the extracellular concentration of the CRH or CRH-related peptide available for interaction with CRH-R1α. The final effect is the inhibition of biological activity, as demonstrated by the decreases in cAMP production presented in the upper panel of the FIG. 7C. On the other hand, the CRH-R1h isoform would bind the receptor ligand (CRH) and stimulate cAMP production by the alpha isoform, through either stabilization of the ligand or induction of receptor dimerization. The final effect of this latter interaction is the stimulation of biological activity, as demonstrated by the decrease in cAMP production presented in lower right panel of FIG. 7C.

The following references were cited herein:
1. Perrin, et al., (1999) Corticotropin releasing factor receptors and their ligand family. *Ann NY Acad Sci* 885, 312–328
2. Chen, R., Lewis, K. A., Perrin, M. H., and Vale W. W. (1993) Expression cloning of a human corticotropin-releasing-factor receptor. *Proc. Natl. Acad. Sci. USA* 90, 8967–8971
3. Liaw, et al., (1996) Cloning and characterization of the human corticotropin-releasing factor-2 receptor complementary deoxyribonucleic acid. *Endocrinology* 137, 72–77
4. Chang, et al., (1993) Identification of a seven transmembrane helix receptor for corticotropin-releasing factor and sauvagine in mammalian brain. *Neuron* 11, 1187–1195. *J. Clin. Endocrinol. Metab.* 85, 3575–3581
5. Perrin, et al., (1995) Identification of the second corticotropin-releasing factor receptor gene and characterization of a cDNA expressed in heart. *Proc. Natl. Acad. Sci. USA* 92, 836–840
6. Lovenberg, et al., (1995) Cloning and characterization of a functionally distinct corticotropin-releasing factor receptor subtype from rat brain. *Proc. Natl. Acad. Sci. USA* 92, 836–840
7. Vita, et al., (1993) Primary structure and functional expression of mouse pituitary and human corticotropin releasing factors receptors. *FEBS Lett* 335, 1–5
8. Stenzel, P., Kesterson, R., Yeung, W., and Cone, R. D. (1995) Identification of a novel murine receptor for corticotropin-releasing hormone expressed in the heart. *Mol. Endocrinol.* 9, 637–645
9. Kishimoto, T., Pearse, R. V., Lin, C. R., and Rosenfeld, M. G. (1995) A sauvagine/corticotropin-releasing factor receptor expressed in heart and skeletal muscle. *Proc. Natl. Acad. Sci. USA* 92, 1108–1112
10. Dautzenberg, F. M., Dietrich, K., Palchaudhuri, M. R., and Spiess J., (1997) Identification of two corticotropin-releasing factor receptors from *Xenopus laevis* with high ligand selectivity: unusual pharmacology of the type 1 receptor. *J. Neurochem.* 69, 1640–1649
11. Arai, et al., (2001) Characterization of three corticotropin-releasing factor receptors in catfish: a novel third receptor is predominantly expressed in pituitary and urophysis. *Endocrinology* 142, 446–454
12. Chalmers, et al., (1996) Corticotropin-releasing factor receptors: from molecular biology to drug design. *Trends Pharm. Sci.* 17, 166–172
13. Spiess, et al., (1998) Molecular properties of the CRF receptor. *Trends Endocrinol. Metab.* 9, 140–145
14. Sakai, et al., (1998) The genomic organization of the human corticotropin-releasing factor type-1 receptor. *Gene* 219, 125–130
15. Ross, et al., (1994) A variant of the human corticotropin-releasing factor (CRF) receptor: cloning, expression and pharmacology. *Biochem. Biophys. Res. Commun.* 205, 1836–1842
16. Grammatopoulos, et al., (1999) A novel spliced variant of the type 1 corticotropin-releasing hormone receptor with a deletion in the seventh transmembrane domain present in the human pregnant term myometrium and fetal membranes. *Mol. Endocrinol.* 13, 2189–2202
17. Perrin, M. H., Sutton, S., Bain, D., Berggren, W. T., and Vale, W. W. (1998) The first extracellular domain of corticotropin-releasing factor-R1 contain major binding determinants for urocortin and astressin. *Endocrinology* 139, 566–570
18. Wille, et al., (1999) Identification of amino acids in the N-terminal domain of corticotropin-releasing factor receptor 1 that are important determinants of high-affinity ligand binding. *J. Neurochem.* 72, 388–395
19. Nabhan, et al., (1995) The alternative spliced type II corticotropin-releasing factor receptor, stably expressed in LLCPK-1 cells, is not well coupled to the G proteins. *Biochem. Biophys. Res. Com.* 212, 1015–1021
20. Slominski, et al., (2000) Corticotropin releasing hormone and proopiomelanocortin involvement in the cutaneous response to stress. *Physiol. Rev.* 80, 979–1020
21. Slominski, A., and Wortsman, J. (2000) Neuroendocrinology of the skin. *Endocrine Rev.* 21, 457–487
22. Slominski, et al., (1999) Cutaneous expression of CRH and CRH-R: is there a "skin stress system"? *Ann. NY Acad. Sci.* 885, 287–311
23. Slominski, A., et al., (2000) The skin produces urocortin. *J. Clin. Endocrinol. Metab.* 85, 815–823
24. Slominski, A et al., (2001) Cutaneous expression of corticotropin releasing hormone (CRH), urocortin and CRH receptors. *FASEB J.*, 15, 1678–1693
25. Quevedo, M. A., Slominski, A., Pinto, W., Wei, E., and Wortsman, J. (2001). Pleiotropic effects of corticotropin releasing hormone (CRH) on normal human keratinocytes. In Vitro Cell Develop. Biol. 37A, 50–54
26. Slominski, A., et al., (2000) Corticotropin releasing hormone (CRH) and related peptides can act as bioregulatory factors in human keratinocytes. *In Vitro Cell Develop. Biol.* 36, 211–216
27. Slominski et al., (1996) The expression of proopiomelanocortin (POMC) and of corticotropin releasing hormone receptor (CRH-R) genes in mouse skin. *Biochem. Biophys. Acta* 1289, 247–251
28. Slominski, A., Costantino, R., Wortsman, J., Paus, R., Ling, N. (1992) Melanotropic activity of gamma MSH peptides in melanoma cells. *Life Sci.* 50, 1103–1108

29. Slominski, A., Ermak, G., and Wortsman, J. (1999) Modification of melanogenesis in cultured human melanoma cells. *In Vitro Cell. Develop. Biol.* 35, 564–565
30. Abdel-Malek, et al., (1995) Mitogenic and melanogenic stimulation of normal human melanocytes by melanotropic peptides. *Proc. Natl. Acad. Sci. U.S.A* 92, 1789–1793
31. Robbins, M., and McKinney, M. (1992) Transcriptional regulation of neuromodulin (GAP-43) in mouse neuroblastoma clone N1E-115 as evaluated by RT/PCR method. *Mol. Brain Res.* 13, 83–92
32. Tsai-Morris, et al., (1996) The genomic structure of the rat corticotropin releasing factor receptor a member of the class II G protein-coupled receptors. *J. Biol. Chem.* 271, 14519–14525
33. Liaw, et al., (1997) Localization of ligand-binding domains of human corticotropin-releasing factor receptor: a chimeric receptor approach. *Mol. Endocrinology* 11, 980–985
34. Smith, S. W., and Valcarcel, J. (2000) Alternative pre-mRNA splicing: the logic of combinatorial control. *Trends Biol. Sci.* 25, 381–387
35. Black, D. L. (2000) Protein diversity from alternative splicing: a challenge for bioinformatics and post-genome biology. *Cell* 103, 363–370
36. Sorek, R., and Amitai M. (2001) Piecing together the significance of splicing. *Nature Biotech.* 19, 196
37. International Human Genome Sequencing Consortium (2001) *Nature* 409, 860–921
38. Black. D. L. (1998) Splicing in the inner ear: a familiar tune, but what are the instruments? *Neuron* 20, 165–168
39. Arts, et al., (2000) Mutations affecting mRNA splicing are the most common molecular defects in patients with neurofibromatosis type 1. *Hum Mol Genet.* 9, 237–247
40. Hinuma, et al., (1997) Human CRF2 receptor protein, its production and use. Patent: JP 1997070289-A
41. Slominski, A., and Paus, R. (1993) Melanogenesis is coupled to murine anagen: Toward new concepts for the role of melanocytes and the regulation of melanogenesis in hair growth. *J. Invest. Dermatol.* 101, 90S-97S
42. Owens, Jr. A. H., Coffey, D. S., and Baylin, S. B., editors. (1982) Tumor Cell Heterogeneity. Academic Press, New York
43. Pawelek, et al., (1992) Molecular cascades in UV-induced melanogenesis: A central role for melanotropins? *Pigment Cell Res.* 5, 348–356
44. Slominski, A., and Pawelek, J. (1998) Animals under the sun: effects of UV radiation on mammalian skin. *Clin Dermatol.* 16, 503–515
45. Slominski, et al., (1996) UVB stimulates production of corticotropin releasing factor (CRF) by human melanocytes. *FEBS Lett.* 399, 175–176
46. Slominski, A., Wortsman, J., and Szczesniewski, A. (2000) Liquid chromatography-mass spectrometry detection of corticotropin-releasing hormone and proopiomelanocortin-derived peptides in human skin. *J. Clin. Endocrinol. Metab.* 85, 3575–3581
47. Slominski, et al., (1988) Metabolism of serotonin to N-acetylserotonin, melatonin, and 5-methoxytryptamine in hamster skin culture. *J. Biol. Chem.* 271, 12281–12286
48. Bomirski, A., Slominski, A., and Bigda, J. (1988) The natural history of a family of transplantable melanomas in hamsters. *Cancer Metastasis Rev.* 7, 95–118
49. Slominski, et al., (1988) Positive regulation of melanin pigmentation by two key substrates of the melanogenic pathway, l-tyrosine and l-dopa. *J. Cell Sci.* 89, 287–296
50. Guest, et al., (2000) Identification and characterization of a truncated variant of the 5-hydroxytryptamine (2A) receptor produced by alternative splicing. *Brain Res.* 876, 238–244.
51. Wood, J. M., Jimbow, K., Boissy, R. E., et al., (1999) What's the use of generating melanin? *Exp. Dermatol.* 8, 153–164

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An isolated corticotropin releasing hormone receptor type 1 protein comprising the amino acid sequence SEQ ID No: 5.

2. A pharmaceutical composition comprising the corticotropin releasing hormone receptor type 1 protein of claim 1 and a pharmaceutically acceptable carrier.

* * * * *